(12) United States Patent
Boyd et al.

(10) Patent No.: US 8,805,509 B2
(45) Date of Patent: Aug. 12, 2014

(54) COMPRESSIBLE ELECTRODES

(75) Inventors: Graham Peter Boyd, Chester (GB); Ian Gregson, Wigan (GB); Julia Heather Herbert, Rosendale (GB)

(73) Assignee: Femeda Limited, Wynyard (GB)

( * ) Notice: Subject to any disclaimer, the term of this patent is extended or adjusted under 35 U.S.C. 154(b) by 1009 days.

(21) Appl. No.: 12/094,948

(22) PCT Filed: Nov. 24, 2006

(86) PCT No.: PCT/EP2006/011288
§ 371 (c)(1),
(2), (4) Date: Jan. 21, 2009

(87) PCT Pub. No.: WO2007/059990
PCT Pub. Date: May 31, 2007

(65) Prior Publication Data
US 2009/0228064 A1   Sep. 10, 2009

(30) Foreign Application Priority Data

Nov. 24, 2005 (GB) .................................. 0523916.5

(51) Int. Cl.
*A61N 1/32* (2006.01)
(52) U.S. Cl.
USPC .......................................................... 607/41
(58) Field of Classification Search
USPC ............ 600/373; 607/41, 115–116, 138, 148, 607/39
See application file for complete search history.

(56) References Cited

U.S. PATENT DOCUMENTS

| | | |
|---|---|---|
| 3,640,284 A | 2/1972 | Langis |
| 3,650,275 A | 3/1972 | Von Der Mozel |
| 3,800,800 A | 4/1974 | Garbe et al. |
| 3,933,147 A | 1/1976 | Du Vall |
| 3,943,938 A | 3/1976 | Wexler |
| 3,973,571 A | 8/1976 | Suhel |
| 4,106,511 A | 8/1978 | Erlandsson |
| 4,580,578 A | 4/1986 | Barsom |

(Continued)

FOREIGN PATENT DOCUMENTS

| | | |
|---|---|---|
| DE | 3518317 | 11/1986 |
| DE | 3827232 | 11/1989 |

(Continued)

OTHER PUBLICATIONS

International Search Report issued in corresponding International Application No. PCT/EP2006/011288 filed Nov. 24, 2006.

(Continued)

*Primary Examiner* — Rex R Holmes
(74) *Attorney, Agent, or Firm* — Knobbe, Martens, Olson & Bear, LLP

(57) ABSTRACT

A compressible electrode for the stimulation of the musculature of the pelvic floor complex e.g. for the treatment of anterior and posterior pelvic floor muscle dysfunction, is reversibly compressible and has electro-conductive elements. The compressible electrode may be used with all the usual control units and treatment regimes for the electro-stimulation of the musculature and nerves of the vagina and/or anus. The compressible electrode may be inserted into the vagina or anus through the use of an applicator. In the compressed state the compressible electrode may be of tampon proportions and after use may easily be removed.

44 Claims, 10 Drawing Sheets

(56) References Cited

U.S. PATENT DOCUMENTS

| | | |
|---|---|---|
| 4,688,575 A | 8/1987 | Duvall |
| 4,785,828 A | 11/1988 | Maurer et al. |
| 4,873,996 A | 10/1989 | Maurer |
| 4,881,526 A | 11/1989 | Johnson et al. |
| 4,909,263 A | 3/1990 | Norris |
| 4,911,149 A | 3/1990 | Borodulin et al. |
| 5,045,079 A | 9/1991 | West |
| 5,046,511 A | 9/1991 | Maurer et al. |
| 5,063,929 A | 11/1991 | Bartelt et al. |
| 5,117,840 A | 6/1992 | Brenman et al. |
| 5,199,443 A | 4/1993 | Maurer et al. |
| 5,314,465 A | 5/1994 | Maurer et al. |
| 5,370,671 A | 12/1994 | Maurer et al. |
| 5,376,206 A | 12/1994 | Maurer et al. |
| 5,385,577 A | 1/1995 | Maurer et al. |
| 5,456,709 A | 10/1995 | Hamedi |
| 5,516,396 A | 5/1996 | Maurer et al. |
| 5,562,717 A * | 10/1996 | Tippey et al. ............. 607/41 |
| 5,571,118 A | 11/1996 | Boutos |
| 5,618,256 A | 4/1997 | Reimer |
| 5,662,699 A | 9/1997 | Hamedi et al. |
| 5,667,615 A | 9/1997 | Maurer et al. |
| 5,702,428 A | 12/1997 | Tippey et al. |
| 5,759,471 A | 6/1998 | Malewicz |
| 5,800,501 A * | 9/1998 | Sherlock ............. 607/138 |
| 5,800,502 A | 9/1998 | Boutos |
| 5,816,248 A | 10/1998 | Anderson et al. |
| 5,871,533 A | 2/1999 | Boutos |
| 5,875,778 A | 3/1999 | Vroegop |
| 5,881,731 A | 3/1999 | Remes |
| 5,921,944 A | 7/1999 | Borodulin |
| 6,063,045 A | 5/2000 | Wax et al. |
| 6,086,549 A | 7/2000 | Neese et al. |
| 6,185,465 B1 * | 2/2001 | Mo et al. ............. 607/138 |
| 6,240,315 B1 | 5/2001 | Mo |
| 6,264,582 B1 | 7/2001 | Remes |
| 6,289,245 B1 | 9/2001 | Mo |
| 6,321,116 B1 | 11/2001 | Mo |
| 6,432,037 B1 | 8/2002 | Eini et al. |
| 6,470,219 B1 | 10/2002 | Edwards et al. |
| 6,631,297 B1 | 10/2003 | Mo |
| 6,865,423 B2 | 3/2005 | Oldham |
| 2002/0000233 A1 | 1/2002 | Jude |
| 2002/0068900 A1 | 6/2002 | Barnes |
| 2003/0004553 A1 | 1/2003 | Grill et al. |
| 2003/0083590 A1 | 5/2003 | Hochman et al. |
| 2003/0087734 A1 | 5/2003 | Kring |
| 2003/0135245 A1 | 7/2003 | Campos |
| 2003/0220589 A1 | 11/2003 | Leivseth et al. |
| 2004/0030360 A1 | 2/2004 | Eini et al. |
| 2004/0054392 A1 | 3/2004 | Dijkman |
| 2004/0122341 A1 | 6/2004 | Walsh |
| 2004/0236385 A1 | 11/2004 | Rowe |
| 2005/0228316 A1 | 10/2005 | Morgenstern |

FOREIGN PATENT DOCUMENTS

| | | |
|---|---|---|
| DE | 3919453 | 12/1989 |
| DE | 4035267 | 5/1991 |
| DE | 4022074 | 2/1992 |
| DE | 4436634 | 4/1996 |
| DE | 19715870 | 10/1998 |
| DE | 19755243 | 6/1999 |
| DE | 10162484 | 7/2003 |
| EP | 0088173 | 9/1983 |
| EP | 178514 | 4/1986 |
| EP | 0263466 | 4/1988 |
| EP | 0 411 632 | 2/1991 |
| EP | 473131 | 3/1992 |
| EP | 638329 | 2/1995 |
| EP | 1279413 | 1/2003 |
| EP | 1704892 | 9/2006 |
| FR | 2547203 | 12/1984 |
| FR | 2655271 | 6/1991 |
| FR | 2709252 | 3/1995 |
| FR | 2709422 | 3/1995 |
| FR | 2754717 | 4/1998 |
| FR | 2757070 | 6/1998 |
| FR | 2767481 | 2/1999 |
| FR | 2806634 | 9/2001 |
| FR | 2827520 | 1/2003 |
| GB | 1480103 | 7/1977 |
| GB | 1599466 | 10/1981 |
| GB | 2 404 339 | 2/2005 |
| JP | 1234567 | 5/1997 |
| JP | 9122248 | 5/1997 |
| JP | 11019223 | 1/1999 |
| JP | 2006167385 | 6/2006 |
| NL | 8902023 | 8/1989 |
| WO | WO8401515 | 4/1984 |
| WO | WO 84/03211 | 8/1984 |
| WO | WO9214510 | 9/1992 |
| WO | WO9324176 | 12/1993 |
| WO | WO9731679 | 9/1997 |
| WO | WO 97/47357 | 12/1997 |
| WO | WO9748446 | 12/1997 |
| WO | WO 98/34677 | 8/1998 |
| WO | WO9935986 | 7/1999 |
| WO | WO0006246 | 2/2000 |
| WO | WO0062699 | 10/2000 |
| WO | WO 01/60446 | 8/2001 |
| WO | WO 01/95829 | 12/2001 |
| WO | WO0209805 | 2/2002 |
| WO | WO 03/007862 | 1/2003 |
| WO | WO2005077276 | 8/2005 |

OTHER PUBLICATIONS

International Search Report issued in corresponding PCT International Application No. PCT/EP2006/011286 on Mar. 8, 2007.

Ohlsson, et al., "Miniaturised Device for Long-Term Intravaginal Electrical Stimulation for the Treatment of Urinary Incontinence," Medical and Biological Engineering and Computing, vol. 26, No. 5, Sep. 1, 1988, pp. 509-515.

International Search Report issued in corresponding International Application No. PCT/EP2006/011287 filed Nov. 24, 2006.

Jeyaseelan, S.M. et al., "An evaluation of a new pattern of electrical stimulation as a treatment for urinary stress incontinence: a randomized, double-blind, controlled trial", Clinical Rehabilitation, 2000, pp. 631-640, 14, SAGE Publications.

* cited by examiner

COMPRESSIBLE ELECTRODES

RELATED APPLICATIONS

This application is the U.S. National Phase under 35 USC §371 of International Application No. PCT/EP2006/011288, filed Nov. 24, 2006, which claims priority to British Application No. 0523916.5, filed Nov. 24, 2005.

FIELD OF INVENTION

The present invention relates to electrical nerve and muscle stimulation and to compressible electrodes and methods for the use of such compressible electrodes and in particular to compressible electrodes and methods for their use in the electro-medical treatment and electro-stimulation of the muscle and nerve groups associated with pelvic floor musculature and especially although not exclusively where there is dysfunction with this musculature resulting in urinary and/or faecal incontinence.

BACKGROUND ART

Caring for women with pelvic floor disorders has become an increasingly important component of women's healthcare. These disorders, which include urinary and faecal incontinence, sexual dysfunction as well as pelvic organ prolapse, affect a large segment of the adult female population. One common cause is trauma during vaginal delivery which may result in a variety of pelvic floor complaints; urinary stress and urge incontinence and faecal incontinence are the most frequent and long lasting.

In order to restore function of the pelvic floor muscles after childbirth, women have been encouraged to perform pelvic floor muscle exercises. Pelvic floor muscle exercises (PFME) are a known treatment for exercising muscles which control the urinary function. The theoretical basis of using pelvic floor muscle exercise for the treatment and prevention of stress urinary incontinence is based on the muscular changes that may occur after specific strength training. A strong and well-functioning pelvic floor can build a structural support for the bladder and the urethra. Postpartum pelvic floor muscle training has been demonstrated to be effective in the prevention and treatment of stress urinary incontinence in the immediate postpartum period. The results also showed that the success of postpartum pelvic floor muscle exercise depended on training frequency and intensity of effort.

Pelvic floor muscle exercises are also called Kegel exercises after Dr. Arnold Kegel, who in the late 1940's, promoted them to strengthen the pelvic floor muscles. The muscles involved in PFME strengthening are the Levator Ani, which include the pubococcygeus, pubovaginalis, puborectalis, iliococcygeus, and also the iliococcygeus muscles collectively these muscles are referred to as the "deep muscles" of the pelvic floor complex. These muscles contract and relax under patient's command allowing the storage and discharge at a socially acceptable time and place, of both urine and faeces. PFME will also activate the "superficial muscles", including ischiocavernosus, bulbospongiousus, the transverse peroneii and the urethral sphincters. Regular exercise is necessary to increase function. Muscle activation promotes function.

Such exercises require the relevant muscles to be contracted and relaxed regularly during the course of a day or over a period of many weeks, often months. A known aid for such exercises comprises a pre-formed core of rigid plastics material. Such aids are provided in a set of graded weights, requiring the (female) patient to insert them into the vagina, and retain them in position. However, this can be difficult for some women. The smallest available weight may be too heavy, or the size is incorrect. For many women the correct positioning of the device is problematic. These devices are not suitable for use by women with moderate or severe genitor-urinary prolapse.

A variety of non-surgical approaches have been investigated as treatments of urinary incontinence, including pelvic PFME, biofeedback, other behavioral therapies, and pelvic floor stimulation. Pelvic floor stimulation (PFS) involves the electrical stimulation of pelvic floor muscles using a probe or skin electrodes wired to a device for controlling the electrical stimulation. It is thought that pelvic floor stimulation via the pudendal nerve and nerve to the Levator Ani will improve urethral closure by activating the pelvic floor musculature. In addition, PFS is thought to improve partially denervated urethral and pelvic floor musculature by enhancing the process of reinnervation. PFS is also thought to improve neuromuscular coordination for the patient enabling them to perform correct voluntary contractions in the future. Patients receiving PFS may undergo treatments in a physician's office or physical therapy facility, or patients may undergo initial training in a physician's office followed by home treatment with a rented or purchased pelvic floor stimulator.

Conventional electro-stimulation treatments for urinary and faecal incontinence require a patient to apply stimulation via an internal electrode or skin electrodes in electrical contact with the body. Electrical stimulation units for home or office use are programmed to deliver stimulation at pre-set frequencies. A conventional electro-stimulation system includes pulse generator housed in a portable battery box that is attached by an appropriate lead to an electrode.

The electro-stimulation systems conventionally use a drive signal to the electrode. Differing therapeutic effects are achieved using different drive signal types. Conventionally such stimulation systems allow for a variation of drive signal pulse width or frequency by the patient. However each such known portable stimulation system has electronics which are dedicated for providing a specific predetermined drive signal having a geometry and other characteristics matched to the intended therapeutic effect. Adjustment of the control signal is conventionally provided by electronic push switches and or rotational control knobs. Such switches and knobs can often be tampered with by the patient, and it is thus difficult for a medical practitioner prescribing electro-stimulation treatment to control the treatment when the patient is away from a clinic.

Other known electro-stimulators include microprocessor based units, but these have a problem that conventionally, specialised pre-programming equipment needs to be used at the clinic to set the signal parameters. Such equipment is expensive and often difficult to use.

In EP 0411632 there is described an expandable vaginal electrode that is adapted to be inserted into a woman's vagina and which is utilized with a controller external to the device and woman's body.

In WO 98/34677 there is described a tampon especially for women suffering from urinary incontinence that is made of sponge like material and is used in the wet state. The tampon is used with a non-insulated electrode and external control source to treat incontinence.

In FR 2762983 there is described a single-use and disposable vaginal or anal endocavity probe. The probe comprises an electrode that is linked to external power supply and control unit and an applicator; the electrode and applicator are non-dissociable.

Whilst there are various devices in the art and available commercially for the treatment of urinary and/or faecal incontinence there is a continuing need for new electrodes that offer effective treatment through effective contact of the electrodes with the muscles to be treated and for electrodes that are comfortable and easy to use.

DISCLOSURE OF THE INVENTION

The present invention and its specific embodiments aim to address the above identified needs and problems associated with conventional plug type electrodes and the problems encountered in the treatment of anterior and posterior pelvic floor muscle dysfunction including prolapse, difficult defecation, sexual dysfunction and incontinence using such electrodes.

In accordance with the present invention there is provided a compressible vaginal or anal electro-stimulation electrode for the neuromuscular electro-stimulation of the musculature of the pelvic floor complex, which comprises a body and at least two electro-conductive elements located at or on the external surface of the body, wherein the body is substantially reversibly compressible in at least one dimension such that the electro-conductive element may be reversibly compressed towards the interior of the electrode body as the electrode is compressed.

The electrode of the present invention is capable of being used in the neuromuscular electro-stimulation of the musculature of the pelvic floor complex via endovaginal (transvaginal) or endoanal (transanal) application and use of the electrode. In the following description reference will be made to the anal or vaginal endocavity. This refers to the location within the anus or vagina at which point the musculature of the pelvic floor complex may be stimulated by the electrode of the present invention.

A key advantage of the compressible electrode of the present invention is that the electro-conductive elements are able to move in conformity with the compression of the electrode and importantly are able to be brought into contact with the walls of the endocavity under pressure. The pressure is due to the resilient nature of the compressible electrode, which once in situ seeks to expand to its pre-compressed state. This ensures that the electro-conductive elements are in contact with the endocavity walls under mild pressure. There is no need for any special additional equipment to expand the electrode to achieve this contact.

The compressible electrode may be used with an external power source and control system.

The body of the electrode is compressible in at least one dimension. The dimensions of the electrode in its non-compressed form are such that one or more of its external surfaces and the electro-conductive elements at or on the surface of the electrode body will be in contact with one or more surfaces of the vaginal or anal endocavity. The electrode in-situ will typically be in a partially compressed state. This state being induced by contact of the electrode surfaces with the surfaces of the endocavity. In this state one or more of the external surfaces of the electrode and the electro-conductive elements at or on the surface of the electrode body are in intimate contact with one or more surfaces of the endocavity. They are forced into contact with the endocavity surfaces by the resilient force induced by the materials used to manufacture the electrode body and/or due to the internal structure of the electrode. Normally, an electrode of these dimensions could not easily be inserted into the vagina or anus for use. However as the electrode of the present invention is reversibly compressible the dimensions of the electrode may be reduced to the required dimensions for easy insertion. The extent of compressibility is such that the electrode may be compressed to a size such that it may be easily inserted into the vaginal or anal endocavity Preferably, the dimensions of the body of the electrode, the choice of material for the manufacture of the body of the electrode and/or the structure of the body of the electrode are such that when the electrode is in-situ the surface of the electrode body and the electro-conductive elements at or on the surface of the electrode body are forced e.g. under pressure, against one or more surfaces of the endocavity. Preferably the electrode body is manufactured from one or more resiliently deformable materials. Thus the body of the electrode being resiliently deformable for insertion is, after insertion and in-situ, able to expand in order to conform to the shape of vaginal or anal endocavity. In-situ the electrode is able to change its shape to substantially conform to change in the shape of the endocavity during use of the electrode and so the electrode is conformable during use. It should be understood that the dimensions described in detail below are for electrodes designed for use in the vaginal endocavity. Electrodes suitable for use in the anal endocavity will be of smaller dimensions due to the smaller size of that endocavity compared to that of the vagina.

In a further embodiment the electrode body may be compressible due to a combination of the choice of materials used for its manufacture and due to its structure. For example the electrode body may be manufactured from resiliently deformable material and the interior of the electrode body may be hollow. In this embodiment when the electrode is compressed the body material is deformed and the hollow interior may be constricted or collapsed to a smaller volume. This combination may provide for an electrode with a high magnitude of reversible compressibility so that the electrode may be compressed to a significantly smaller volume compared to the non-compressed state.

The material used for the electrode body is preferably a resiliently deformable/compressible biocompatible material and may be formed as a solid or semi-solid mass of a resiliently compressible biocompatible material that allows the electrode body to resiliently deform and to conform to the shape of the object deforming the electrode e.g. the anal or vaginal endocavity or, when used, by the wall of an applicator. The resiliently deformable/compressible biocompatible materials may be selected or tailored to provide any desired degree of deformability/compressibility and/or resilient properties. The material can be selected and adjusted to provide the desired attributes of softness, pillowy, cushiony, and/or firmness and is selected in relationship with the desired level of support required for effective contact with the endocavity walls whilst maintaining an ability to conform to the shape of the anal or vaginal walls. It is preferred that the deformable/compressible device body comprises biocompatible material in the form of compressible/deformable foam. Examples of suitable materials include thermoplastic elastomeric foam materials such as polyvinyl formal foam (PVF). polyurethane foams. In one preferred embodiment the device body is prepared from polyurethane and most preferably from moulded polyurethane foam. These polyurethane foams may be prepared from polyols and isocyanates, which are mixed and injected into a molding tool where they foam and cure.

The foamed electrode body may comprise a closed cell or open cell foam. It is preferred that the foam is open celled. The use of open celled foams is desirable as it provides for good levels of compressibility and deformability. In a preferred embodiment the foam formulation is selected to be self skinning. During manufacture of the electrode body, by injection of a foamable composition into a suitable mold, a skin of material compositionally identical to the composition of the foam of the interior of the body is formed at the surface of the electrode body. It is preferred that the foam of the electrode body has a relatively low density. This ensures maximum compressibility/deformability for ease of insertion into the applicator if used and for insertion into the relevant body endocavity. It is preferred that the foam density is less than 250 $Kgm^{-3}$ preferably less than 200 $Kgm^{-3}$ and most preferably less than 150 $Kgm^{-3}$. It is preferred that the foam density is within the range of from 250 to 80 $Kgm^{-3}$, more preferably within the range from 200 to 80 $Kgm^{-3}$, more preferably within the range from 200 to 100 $Kgm^{-3}$ and most preferably within the range from 150 to 100 $Kgm^{-3}$. In addition to relatively low density it is also preferred that the polymer system used in the manufacture of the foam does not produce a hard foam material, which is strongly resistant to deformation. The polymer system is preferably selected to produce a relatively soft foam material that has relatively low values for IDF (indentation force deflection as measured according to ASTM D 3574). At the same time the materials for manufacture of the electrode body foam should be selected to produce a electrode body foam that is strong enough so that the skinned surface and the bulk of the foam remains intact during manufacture and use of the electrode.

As the electrodes of the present invention may be stored in the compressed state e.g. within an applicator, for extended periods of time the materials used in its manufacture must be stable and retain their properties for the normal shelf-life of the electrode. In particular the resiliently deformable/compressible materials must retain their resilient properties during storage so that when released from compression e.g. when expelled from an applicator they are able to expand to the normal non-compressed state and to exert the required pressure against the walls of the anal or vaginal endocavity. It is also important that the materials used do not leach chemicals e.g. plasticizers etc during storage. The resiliently deformable/compressible material used to prepare the electrode body should exhibit relatively rapid change from the compressed to the non-compressed state, so that on insertion the electrode rapidly expands from the compressed state to make contact with the relevant endocavity. This change from compressed to non-compressed state should ideally occur in a matter of seconds, preferably less than 10 seconds, more preferably less than 5 seconds and most preferably less than 3 seconds.

The compressible electrode of the present invention may comprise a compressible electrode body which has been moulded around the interior components of the compressible electrode to encapsulate them or it may be a compressible electrode body that has been manufactured with a hollow interior into which the interior components may be placed during manufacture of the compressible electrode. In a further embodiment the electrode body may be moulded in two halves preferably by over molding each of the electro-conductive elements; the two halves are then sealed around internal components using such techniques as hot plate welding. The electrode may be manufactured by a combination of any of these methods. It is preferred however that the electrode body is pre-moulded in one piece with cavities, accessible from the exterior, which are capable of receiving and accommodating the electro-conductive elements and an electronic sub-assembly. In a preferred embodiment the moulded electrode body comprises a cavity for an electronic sub-assembly accessible from the distal end of the moulded electrode body and preferably moulded recesses along each side of the electrode body to accommodate electro-conductive elements on each side of the electrode.

In a further embodiment the electrode of the present invention may have and preferably does have a defined shape. In particular the shape of the electrode may be selected to exhibit certain properties in relation to its symmetry. It is preferred that a cross-sectional shape of the electrode, perpendicular to the axis of insertion and when viewed along the axis of insertion, is non-circular. Preferably, the perpendicular cross-section is taken at the mid-point of the electrode along the axis of insertion. Preferably, the shape of the electrode is such, that the shape of any cross-section perpendicular to the axis of insertion is such, that the electrode may not be freely rotated about the axis of insertion when in-situ, whilst at the same time providing the maximum potential contact of the electrode with the walls of the anal or vaginal endocavity. In one embodiment this perpendicular cross-sectional shape may exhibit no planes of reflective symmetry or axis of rotational symmetry e.g. the shape is completely asymmetrical. In one embodiment, whilst being non-circular in cross-section, it is preferred that the perpendicular cross-sectional shape exhibits at least one reflective axis and/or rotational axis of symmetry but not infinite reflective axis or rotational axis of symmetry; thus the perpendicular cross-sectional-shape may be any non-circular shape. In a preferred embodiment the perpendicular cross-sectional shape approximates to a rect-angle or square, which preferably has softened rounded corners being corners that are not angular and do not define a right angle or any defined angle. The extent of rounding of these corners is such that on viewing the electrode in perpendicular cross-section along the axis of insertion it is clear that the perpendicular cross-sectional shape is derived from a broadly rectangular or square shape. Preferably the perpendicular cross-sectional shape is broadly square or rectangular in shape. Preferably the perpendicular cross-sectional shape exhibits at least one axis of reflective symmetry and more preferably at least two axis of reflective symmetry. In the broadly square shaped or rectangular shaped embodiments the perpendicular cross-sectional shape exhibits at least two axis of reflective symmetry and at least one axis of rotational symmetry; the broadly square shaped embodiment having four reflective and one rotational axis of symmetry and the broadly rectangular shaped embodiment having two reflective and one rotational axis of symmetry. The electrode of the present invention may have a shape, such that when the electrode is viewed from the side, that is in profile along the axis of insertion of the electrode, the shape of the side is broadly similar to the shape of the electrode when viewed along the axis of insertion e.g. from the front of the electrode. The electrode, when viewed from above, at approximately 90 degrees to the side view, may exhibit a shape which is of similar or different shape and dimensions to those of the side or front views. In a preferred embodiment the side and top views are of different shape and or dimensions from that of each other and the front view of the electrode. In one embodiment the side view may exhibit no rotational or reflective axis of symmetry. In one embodiment the side view may exhibit one rotational and two reflective axis of symmetry; in a preferred embodiment it exhibits one reflective and no rotational axis of symmetry. In a further embodiment the top view may exhibit no rotational or reflective axis of symmetry. In a further embodiment the top view may exhibit a single rotational and two reflective axis of symmetry; in a preferred embodiment it exhibits one reflective and no rotational axis of symmetry. The electrode may have two distinct ends. The first is proximate to the point of insertion into the anus or vagina and the second is remote from the proximate end or point of insertion. In one embodiment the proximate end is larger in dimensions compared to the remote end of the electrode; the electrode will therefore have a tapered or pear shaped appearance when viewed from either the side or top of the electrode or from both perspectives. It is preferred that dimensions of such a electrode are greater when viewed from the top compared to those when viewed from the side of the electrode so that the electrode may have a slightly flattened appearance when orientated for insertion. Alternatively the dimensions may be reversed with the proximate end having smaller dimensions than the remote end of the electrode.

In one embodiment the dimensions of the electrode body are greater along the axis of insertion compared to the dimensions perpendicular e.g. in cross-section to that axis. In an alternative embodiment the dimensions of the body may be similar in both views.

The compressibility of the electrode is such that it may easily be inserted into the relevant endocavity. The limits of compressibility will be set by the nature of the materials used e.g. resiliently deformable material for the body, by the nature of the internal structure e.g. the presence of hollow cavities and also the dimensions of any electronic components that may be used internally. Ideally these are selected to afford the maximum amount of compressibility for the electrode. In one embodiment the electrode may be compressed to dimensions that are different in proportion relative to each other compared to the same dimensions in the non-compressed state. In a further embodiment the electrode may be compressible to the same or similar extent in all dimensions. In a further embodiment the electrode has greater compressibility in the plane perpendicular to the axis of insertion of the electrode. The electro-stimulation electrode may have two dimensions perpendicular to the axis of insertion that have different degrees of compressibility. For example in the non-compressed state the electrode may have a length of approximately 60 to 65 mm and a height of approximately 30 to 45 mm and a width of approximately 30 to 45 mm. On compression the compressed electrode may have a length of approximately 60 to 65 mm, a height of approximately 25 mm and a width of approximately 15 mm. In the non-compressed state the electrode may have a length in the range of from approximately 30 to 120 mm, preferably approximately 40 to 100 mm, more preferably approximately 45 to 75 mm and most preferably approximately 45 to 65 mm. In the non-compressed state the electrode may have at least two equal dimensions or at least two non-equal dimensions perpendicular to the axis of insertion that are within the range of approximately 30 to 60 mm, preferably approximately 35 to 55 mm and most preferably approximately 35 to 50 mm. Preferably the length of the electrode in the non-compressed state is equal to the length of the electrode in the compressed state. The materials selected for the manufacture of the electrode and/or the structure of the electrode are such that at least one of the dimensions of the electrode perpendicular to the axis of insertion may be reduced on compression by at least 20%, more preferably at least 40%, more preferably at least 50% and most preferably at least 60%. All of the dimensions of the electrode perpendicular to the axis of insertion may be reduced on compression by at least 15%, preferably at least 25%, more preferably at least 35% and most preferably by at least 40%. In the compressed state the dimensions of the electrode perpendicular to the axis of insertion may be such that the width is in the range of 10 to 35 mm, preferably 10 to 30 mm, preferably 10 to 25 mm and most preferably 15 to 20 mm and the height of the compressed electrode is within the range of 10 to 40 mm, preferably 10 to 35 mm, more preferably 10 to 30 mm and most preferably within the range of 15 to 30 mm. It is preferred that the electrode has sufficient compressibility such that the volume of the electrode in the compressed state is reduced by at least 20% compared to that in the non-compressed state, preferably it is reduced by at least 25%, more preferably it is reduced by at least 30%, more preferably it is reduced by at least 40%, more preferably it is reduced by at least 50%, and most preferable by at least 75%.

In a further embodiment the electrode of the present invention may be made of materials and constructed in such a way that it may be compressed into a shape that approximates to a tampon form. In this form it is easier to insert into the vagina or anus. Once inserted and in place the electrode in tampon form will expand and come into contact with the walls of the vaginal or anal endocavity.

Thus the electrode of the present invention may be adapted for deployment into an anal or vaginal endocavity via the use of an applicator. The applicator may for example be a hollow tubular applicator containing the electrode in its bore in the compressed state. The electrode is deployed from the applicator into the vagina or anus. Typically the applicator including compressed electrode is positioned at the vaginal introitus (opening) or anal sphincter and the electrode is then discharged from the applicator into the anus or vagina by operation of the plunger. Once inside the vagina or anus the compressed electrode may expand.

The present invention also provides for an electrode for the stimulation of the musculature of the pelvic floor complex e.g. for the treatment of anterior and posterior pelvic floor muscle dysfunction, which comprises an electrode according to the present invention in combination with an applicator. Preferably the applicator comprises an outer member and an inner member, the electrode being located within the outer member.

In this embodiment the outer member is adapted to house the electrode and the inner member. The inner member is located and movable within the bore of the outer member and co-operates with the outer member to force the discharge the electrode from the bore of the outer member, after the applicator has been positioned at the vaginal introitus (opening) or anal sphincter.

The applicator may be marked, indented or grooved in such a way that the orientation for insertion is obvious to the user.

Apart from the electrode body the compressible electrode comprises at least two electro-conductive elements. All other components normally required to enable use of the electrode for electro-stimulation e.g. power source and circuitry/signal generating means for generating and controlling the generation of electrical pulses, are located outside of the electrode body and therefore during use are outside the body of the user. The electrode may be connected to these components and is in communication with these components through an appropriate cable e.g. wire and/or connectors.

The electro-conductive elements may be provided upon and attached to the surface of the electro-stimulation electrode and connected to the interior via appropriate conductive paths e.g. wiring. Alternatively, the electro-conductive elements may be formed as part of the interior components of the electro-stimulation electrode and may be exposed at the surface of the body of the electro-stimulation electrode through appropriately defined orifices in the electrode body. It is preferred that the electro-conductive elements are preformed and are not formed as part of the interior components but are capable of being attached thereto or to conductive elements in communication with the interior components. The electro-conductive elements may be made of a bio-compatible conductive material such as:—stainless steel, conductive rubber, conductive plastic, sputtered plastic or electro plated plastic etc. Suitable examples of electrode material are conductive styrene butadiene styrene (SBS) materials; the conductivity being imparted by carbon filer. The conductive SBS electrodes may be manufactured by injection moulding or extrusion. In one embodiment the preferred electrode material is conductive ethylene vinyl acetate (EVA); this material helps to reduce stiction between the electrode and the applicator when used. Another suitable material is conductive silicone rubber. The size and shape of the electro-conductive elements may be such that they cover or are exposed at most of the exterior surface of the electrode body. They may be of any shape or size save that there is a need for enough space between the elements to prevent shorting of the electrode. In one embodiment the electro-conductive elements are approximately rectangular in shape and are of approximate dimensions of 28 mm×13 mm. In this embodiment they are located at or upon opposite surfaces of the electro-stimulation electrode approximately 180 degrees apart. The purpose of these electro-conductive elements is to conduct a waveform from the electro-stimulation electrode to the musculature of the pelvic floor complex. In one preferable embodiment the electro-conductive elements are in plate form. In a further embodiment the electro-conductive elements may be annular in which case there are two annular electro-conductive elements forming two continuous bands around a circumference of the electro-stimulation electrode; preferably this is the circumference that is perpendicular to the axis of insertion. The electro-conductive elements may be manufactured from material that may deform in co-operation with the deformation of the electrode body. In an alternative embodiment the electro-conductive elements may be located on resiliently deformable arms that communicate with the interior of the electrode and which are compressed as the electro-stimulation electrode is compressed. The electro-conductive elements may be sprung to maintain correct pressure on the wall of the vaginal or anal endocavity during use. In a further embodiment the electro-conductive elements comprise a clipping mechanism that enables the conductive elements e.g. wiring, inside the electrode to be clipped to the electro-conductive elements and thereby electrically connect them to the internal wiring in the electrode body. In one embodiment the conductive element is integrally moulded with the electro-conductive elements.

In one embodiment the electro-conductive elements are part of an assembly which comprises an electrode component and electrode chassis. The chassis may contain some components that are required to secure the wiring for and to the electrode. The chassis may be used to house or locate a point contact in the compressible electrode body for coupling with appropriate connectors and/or cabling to external control units. The electro-conductive elements as part of an electrode component may be connected directly to this chassis by one or more resilient members that allow the electro-conductive elements to be compressed towards the chassis. The resilient nature of these members ensuring that when the pressure is released after compression of the electrode then the electro-conductive elements may return to their pre-compressed relationship to the chassis. In one embodiment the electrode components have electrode pads that may be broadly rectangular in shape. Each pad has an electro-conductive surface which is exposed on assembly of the compressible electrode through openings in the compressible body of the electrode. Each electrode component has a resilient arcuate arm which at one end is connected to or formed with the electrode pad and which at the opposing end is connected to or formed with a flat plate section. The flat plate section is preferably in a plane that is approximately parallel to the plane of the electrode pad. Thus there are effectively two parallel pads connected to each other via an arcuate arm. In a preferred embodiment the arcuate arms are connected to or formed with the pads at one of their narrower edges. The flat plates may be attached to, or located within, or formed with the chassis in such an arrangement that each electro-conductive surface faces away form the chassis and does not face towards other electro-conductive elements. In this way the electro-conductive elements are anchored to a point that will be located within the body of the compressible electrode. In use pressure may be applied to the surfaces of the electro-conductive elements. Under pressure the position of the chassis remains substantially constant within the electrode but the resilient arcuate arms are able to bend relative to the anchor point on the chassis and the electrode pads are able to move towards the chassis. Thus the electrode components may be compressed and moved towards the chassis by the application of pressure to the electrode pads. When the pressure is released the electrode components are able to return to their non-compressed state due to the spring like properties afforded to the components by the resilient deformable nature of the arcuate arms and the nature of their attachment to and their spatial arrangement in relation to the chassis.

With this arrangement it is possible to ensure that the electro-conductive elements are sprung to maintain correct pressure on the walls of the vaginal or anal endocavity during use.

It is also envisaged that in accordance with the present invention the electrodes with or without applicators may be provided as a pack of electrodes.

The present invention further provides for a method for the stimulation of the musculature of the pelvic floor complex e.g. for the treatment of anterior and posterior pelvic floor muscle dysfunction, which method comprises use of an electrode according to the present invention. In a preferred embodiment the method comprises use of an electrode for the stimulation of the musculature of the pelvic floor complex e.g. for the treatment of anterior and posterior pelvic floor muscle dysfunction according to the invention, which utilizes an applicator.

The electrode comprises wiring which exits from the electrode at its distal end. This wiring may be terminated in a standard connector. This section of wiring attached to the electrode may be used to aid removal of the electrode after use.

The external components that may be used with the electrode to generate suitable waveforms and control treatment are well known in the art. In a preferred embodiment the electrode is used with an external treatment device and as part of a treatment system wherein the waveform used is as described in either WO 97/47357 or U.S. Pat. No. 6,865,423, the disclosures of which are hereby incorporated in their entirety by reference. Thus in one embodiment the waveform may comprise two or more components each component being a train of regularly spaced pulses. In one embodiment a second component is combined with the first component but the second component has spacing between successive pulses that is less than the spacing between successive pulses in the first component. In a further embodiment there is a third component that has spacing between successive pulses that is less than the spacing between successive pulses in the second component. In a further embodiment there may be periods of relaxation between sets of pulse trains. In this embodiment it is preferred that the period of relaxation is at least equal to the period of stimulation. The treatment cycle may be over a total period of three hours or less, preferably 2 hours or less, preferably 1 hour or less, and most preferably less than 1 hour. In a particularly preferred embodiment the period for the treatment cycle is 45 minutes or less. The treatment will typically be delivered through a combination of stimulation and rest periods. Each combination is typically 2 minutes or less, preferably 1 minute or less. In one embodiment the stimulation phase is of the order of 10 seconds and the recovery phase is of the order of 50 seconds. In a preferred embodiment the recovery phase is of the same order or greater than that of the stimulation phase and preferably both phases are of the order of 5 to 10 seconds. The first component may have a pulse repetition frequency between 1 and 15 Hz, more preferably between 1 and 6 Hz or between 5 and 15 Hz. The second component may have a pulse repetition frequency between 30 and 60 Hz, more preferably between 40 and 60 Hz. The third component may have a pulse repetition frequency between 80 and 300 Hz, more preferably between 80 and 200 Hz. The pulses may have a pulse width of 50 to 350 microseconds. The pulse width for each component may be of the same magnitude or may be different for each component. The pulse width may be narrow during the early stages of the treatment cycle and then increased gradually or in steps throughout the treatment cycle. Variation of the pulse width in this way may be used as an alternative to pulse amplitude variation or in addition to pulse amplitude variation during the treatment cycle. The amplitude of the pulses for each component may be of the same magnitude or may be different for each component. The pulse amplitude for each component may be of a fixed magnitude throughout the treatment cycle or preferably may be set at one or more magnitudes at one or more periods in the treatment cycle. The pulses may be between 0 and 90 mA. In one preferred embodiment the pulse amplitude is set at a low level initially and is ramped up through the treatment cycle to a higher amplitude. In a preferred embodiment the waveform consists of a series of pulses of approximately 150 to 350 microseconds at a maximum voltage of 60 volts. The electrode may be operated with a control unit such that the output levels of the device are varied automatically over a period of time from zero volts up to the treatment maximum over a period of approximately 45 minutes. This will ensure a safe comfortable start for the treatment cycle and enables comfortable attainment of the maximum output by using the initial accommodation to the lower intensity pulses. The current is preferably applied, regulated and increased through the treatment period of around 20 to 50 minutes, preferably 20 to 45 minutes, more preferably 20 to 40 minutes. Treatment is preferably started at less than 45 mA, more preferably less than 40 mA and rises to 40 mA or more, preferably 45 mA or more for the last ten minutes of the treatment with a series of ramps in between. In one embodiment based on a pulse frequency of 35 Hz and a pulse width of 250 microseconds for example, the current is applied at 6 mA after insertion and rises to 12 mA over the first 10 minutes. Then the current is ramped from 12 mA to 40 mA over the next 10 minutes. Then the current is held at 40 mA over the next 10 to 15 minutes. Thus the profile commences with a low impact on the user and then increases in intensity during the 30-45 minute treatment cycle. This cycle has been found to be particularly useful for use with the electrodes of the present invention.

It is envisaged that the electrode of the present invention may be used in circumstances where there is no recognized dysfunction of the musculature of the pelvic floor complex that has resulted in any symptoms of dysfunction e.g. incontinence. In these circumstances the electrodes of the present invention may be used to improve the performance of the musculature of the pelvic floor complex prior to dysfunction or to assist in preventing dysfunction. As an example women may use the electrodes and in advance of pregnancy to strengthen the musculature of the pelvic floor or to ensure it is in good physical condition prior to pregnancy and child birth.

DESCRIPTION OF THE DRAWINGS

For a better understanding of the invention, and to show how the same may be carried into effect, reference will now be made, by way of example, to various specific embodiments of the invention as shown in the accompanying diagrammatic drawings, in which.

DETAILED DESCRIPTION OF THE INVENTION

Figure 1A:
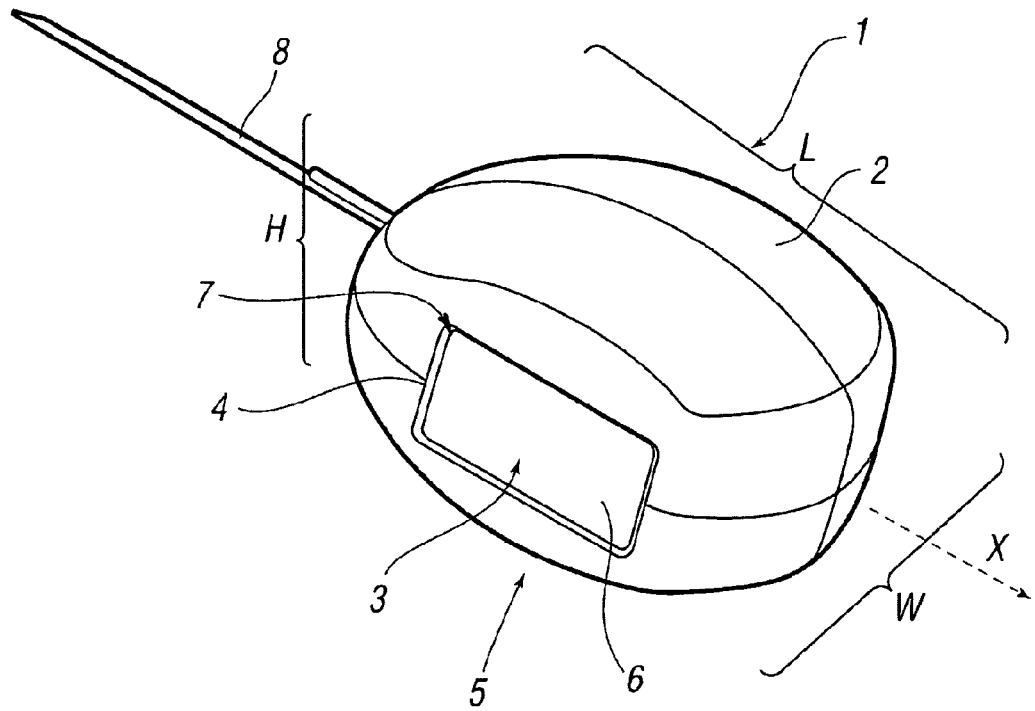
FIG. 1(a) shows in perspective view a compressible electrode according to the present invention, FIG. 1(b) (i) shows a cross-sectional view of the electrode perpendicular to the axis of insertion (x) of the electrode, 1(b) (ii) shows a side view of the electrode and 1(b) (iii) shows a top view of the electrode, FIGS. 2(a) and (b) show in perspective view a compressible electrode according to the present invention in the non-compressed and compressed state, FIGS. 3(a) and (b) show an applicator arrangement for use with the compressible electrode of the present invention, FIGS. 4(a), (b) and (c) show the arrangement of the internal components and electro-conductive elements for use in a compressible electrode according to the present invention and the assembly of the compressible electrode.
Figure 1B:
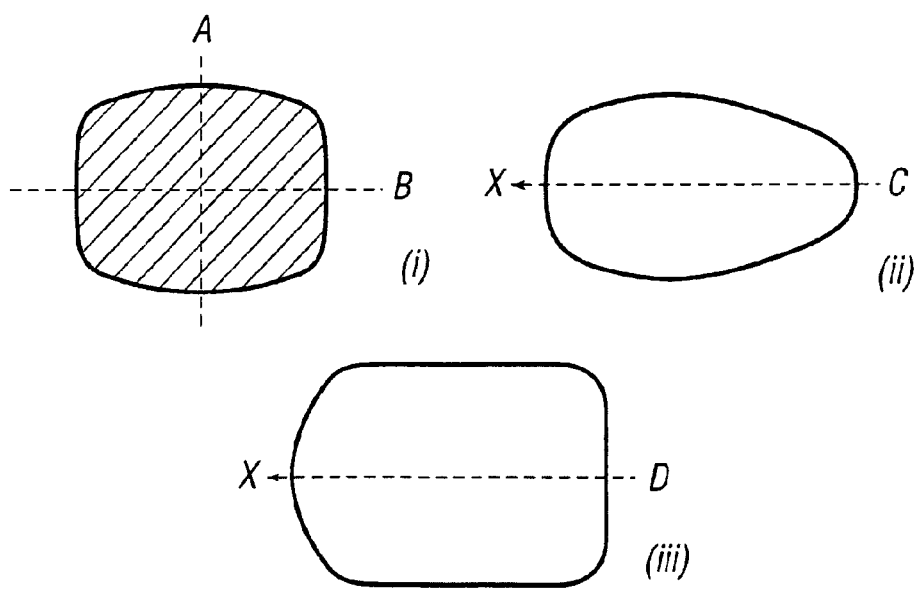

Referring to FIG. 1(a) an electro-stimulation electrode (1) is shown in the non-compressed, fully expanded state. The electrode (1) has a body (2) which has been constructed from bio-compatible resiliently compressible foam. Electro-conductive elements (3 and 3' not shown) emerge from within the body (2) of the electrode and are located at the surfaces (4 and 4' not shown) on sides (5 and 5' not shown) of the electrode (1). The electro-conductive elements (3 and 3' not shown) are relatively flat. In this particular embodiment the electro-conductive elements (3, 3') are in communication with internal components (not shown) of the electrode (1) through internal conductive paths. They pass from within the electrode (1) to provide electrode surfaces (6 and 6' not shown) that are located in approximately the same plane as the surfaces (4, 4') of the sides (5, 5') of the electrode. The main body of the flat electrode components (3, 3') are located below the surface (4, 4') of the body (2) within a hollow cavity (not shown) within the body (2) of the electrode (1). The surfaces (6 and 6' not shown) of the electro-conductive elements (3, 3') appear through these openings (7 and 7' not shown) of the body (2). In one embodiment the electrode components (3, 3') may be surface mounted on the body (2) of the electrode (1); in this embodiment the surface mounted electrode components (3, 3') may be in contact with conductive paths that communicate with the interior of the body (2). The electrode (1) has a wire (8) which passes through a hole (not shown) in the body (2) of the electrode and communicates with and is attached to interior components of the electrode (1) to provide electrical connectivity between the electrode and external control systems and signal generating systems. The dimensions of the electrode (1) which, in the non-compressed state, are such that the length (L) is greater than the width (w), which is in turn greater than the height (h). This electrode (1) is therefore an example of an electrode according to the invention where when viewed in cross-section along the axis of insertion (X) the electrode (1) has a non-uniform symmetrical cross-section with two planes of symmetry. This non-uniformity means that the electrode (1) is less prone to rotation or displacement relative to the axis of insertion (X) during use of the electrode (1). The electrode (1) has no sharp edges whilst having clearly defined surfaces that are connected to each other by gently curving regions. The compressible properties of the electrode (1) ensure resilient contact with the endocavity during use, its overall dimensions and shape, coupled with the smooth curvature of communicating surfaces, enables the electrode (1) to be easily and comfortably inserted during use, whilst at the same time limiting or preventing unwanted rotation and displacement during use. Referring to FIG. 1(b) the cross-sectional shape of the electrode is shown in (i); the cross-section being perpendicular to the axis of insertion (x) of the electrode. Here it can be seen that the shape is broadly rectangular with softened rounded corners. The perpendicular cross-sectional shape exhibits two axes (A and B) of reflective symmetry and a single axis of rotational symmetry along the axis of insertion. Referring to FIG. 1(b) the electrode is shown in side perspective in (ii); here it can be seen that in side profile the electrode has a single axis of reflective symmetry C, which is along the axis of insertion X of the electrode. In side profile there is no rotational axis of symmetry. Referring to FIG. 1(b) the electrode is shown in top perspective in (iii); here it can be seen that in top profile the electrode has a single axis of reflective symmetry D, which lies along the axis of insertion X of the electrode. In top profile there is no rotational axis of symmetry.

Figure 2A:
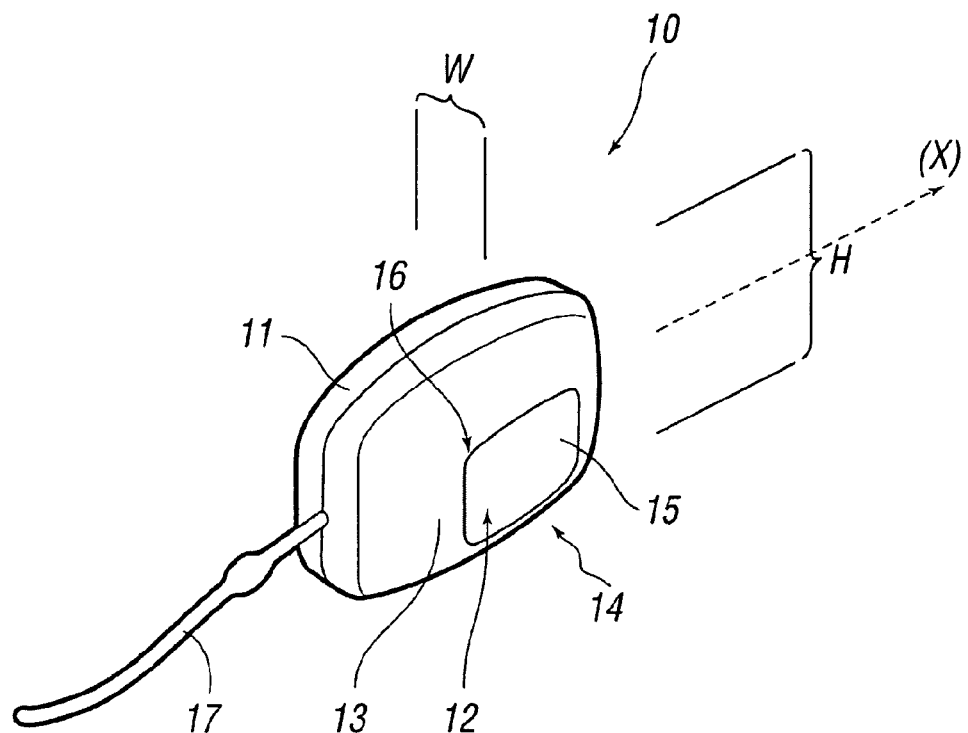
Figure 2B:
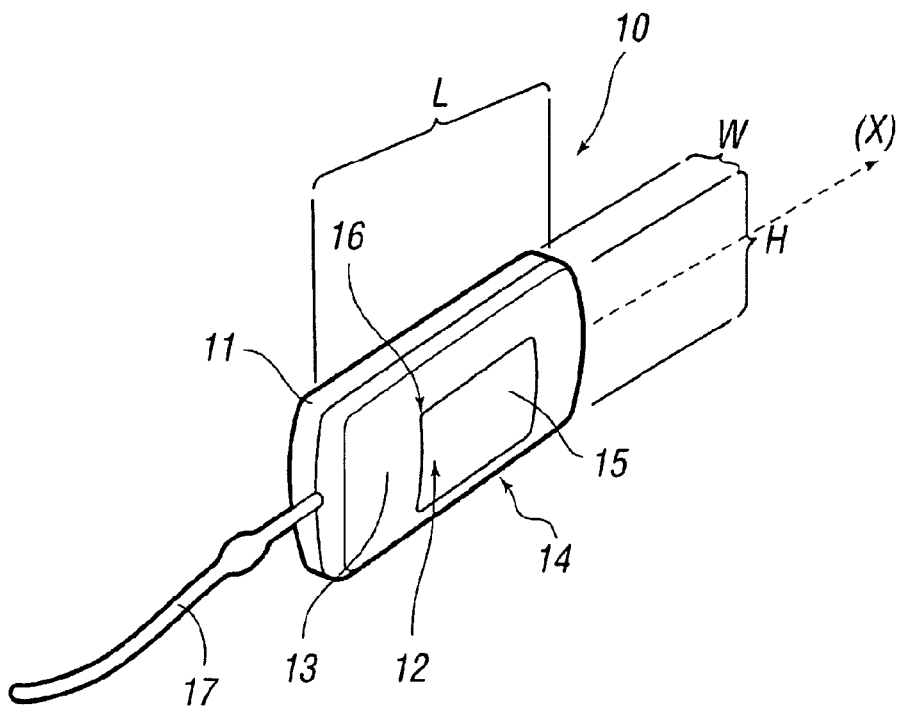
Figure 3A:
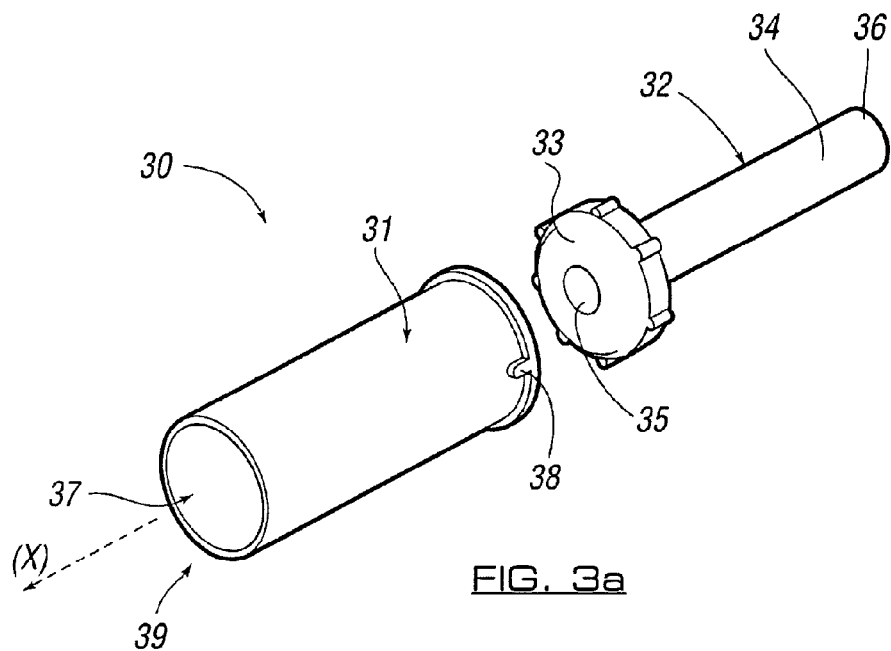
Figure 3B:
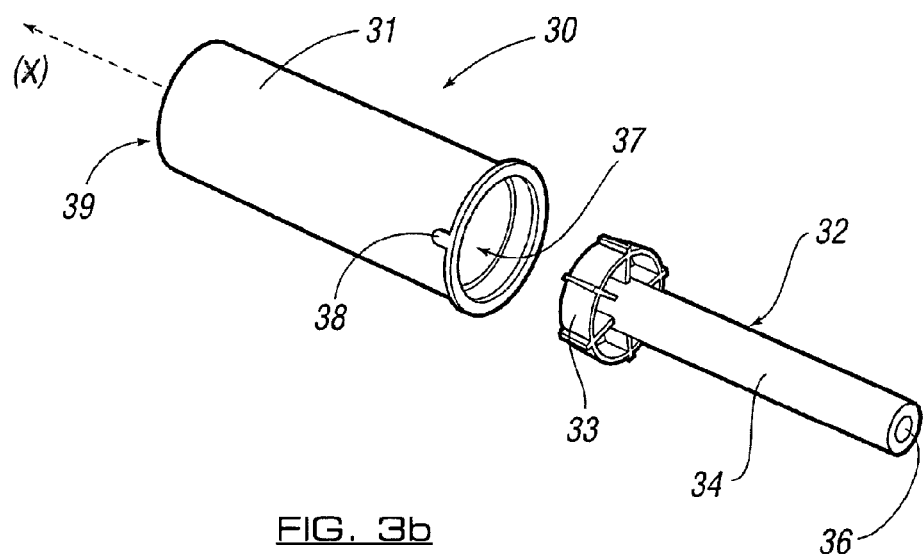

FIGS. 2(a) and (b) show a compressible electrode (10) that whilst being broadly similar in construction to the compressible electrode (1) illustrated in FIG. 1 has a more uniform cross-section and overall appearance. Thus the compressible electrode (10) has a body (11), electro-conductive elements (12 and 12' not shown), body surfaces (13 and 13' not shown) on sides of the compressible electrode (14 and 14' not shown), electro-conductive surfaces (15 and 15' not shown), body openings (16 and 16' not shown) and a wire (17). FIG. 2(a) shows the compressible electrode (10) in the non-compressed state. Here the compressible electrode (10) has a width (W) that at its widest point is about 45 mm and has a height (H) that at its highest point is about 45 mm. The length (L) is about 60 mm. Thus the compressible electrode (10) will have a relatively uniform cross-section at any point along the axis (X) of insertion. However, although the cross-sectional dimensions are approximately uniform the compressible electrode (10), overall, has a shape which has distinct surfaces that are in communication with each other through smooth curves; this shape provides for a cross-section along the axis (X) of insertion that is non-circular. FIG. 2(b) shows the same compressible electrode (10) as shown in FIG. 1(a) but after it has been compressed. Here it is apparent that the length (L) of the compressible electrode (10) has remained broadly unchanged at 60 mm but the height (H) has been reduced to 25 mm and the width (W) has been reduced to 15 mm. The compressed compressible electrode has the overall appearance and dimensions of a Tampon. It should also be noted that this electrode has exhibited non-uniform compression. In this embodiment the electrode in compression is less than 20% of the volume of the electrode in the non-compressed state The electrode (10) in this compressed form is preferably inserted into the vagina or anus by means of an applicator. One suitable form of applicator is illustrated in FIG. 3. Referring to FIGS. 3(a) and (b) there is shown an applicator (30) that has an outer member (31) and an inner member (32). The inner member (32) has a head (33) attached to a handle (34). The inner member (32) has a bore (35) that passes through the inner member (32) and opens at the end (36) of the handle (34). The inner member (32) is able to fit comfortably within the bore (37) of the outer member (31). The outer member (31) has a marker (38) that indicates the correct orientation for use of the applicator (30). When assembled the inner member (32) is located within the bore (37) of the outer member (31) and a compressed electro-stimulation electrode according to the present invention e.g. as illustrated in FIGS. 1 and 2(a) and (b) is located within the bore (37) of the outer member (31) and adjacent the opening (39) of the outer member (31). When located within the bore (37) the compressed electrode is retained in the compressed state. The electrode is orientated within the applicator such that the wire of the electrode (not shown in this Figure) is able to pass along the bore (37) of the outer member (31) through the bore (35) of the inner member (32) and emerge from the end (36) of the inner member (32). Once assembled the applicator (30) with electrode are ready for use. In order to position the electrode in the vagina or anus of a user the outer member (31) of the applicator (30) is placed at the vaginal introitus (opening) or anal sphincter and then the inner member (32) is used to apply pressure to the end of the compressed electrode within the bore (37) of the outer member (32) and to force the electrode out of the bore (37) and into the endocavity of the vagina or anus. As the electrode leaves the bore (37) of the outer member (31) it is no longer held in compression and is able to expand and contact the walls of the vaginal or anal endocavity. The wire passes out of the vagina or anus and may be held and pulled by the user to remove the electrode from the vagina or anus once the treatment cycle is completed. In this embodiment the bore of the outer member will have a cross section on the axis of insertion (X) that is broadly similar in shape to the cross-section of the electrode when in the compressed state.

Figure 4A:
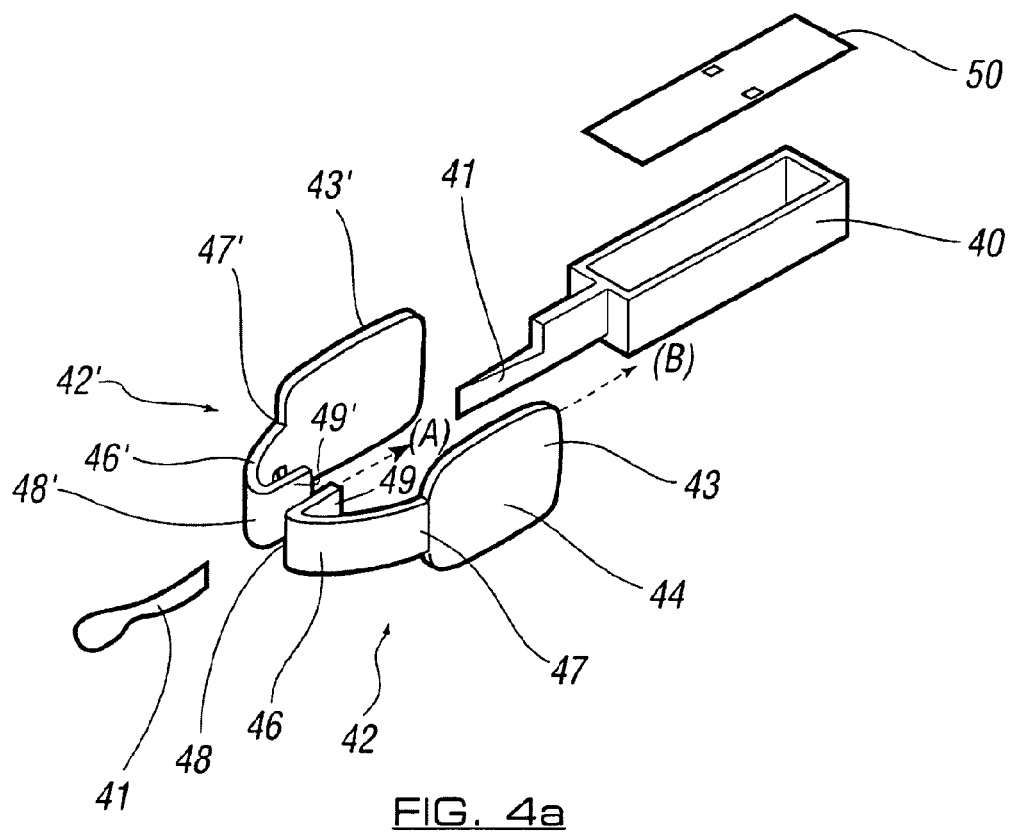
Figure 4B:
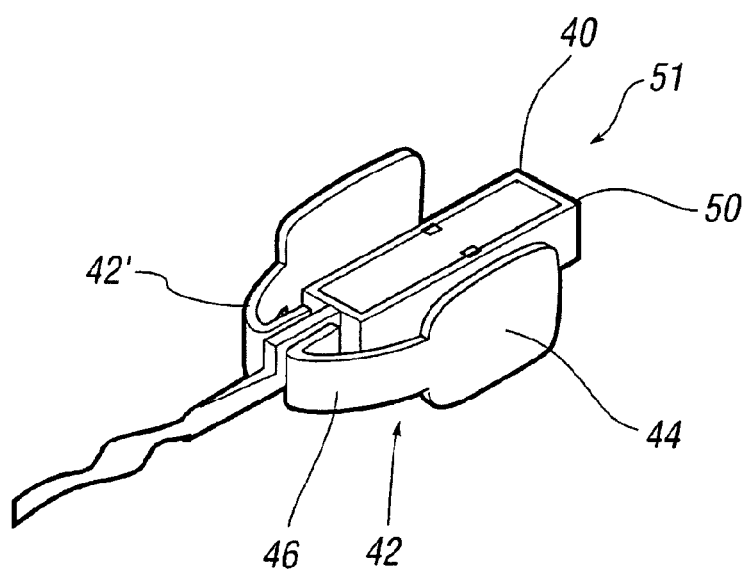
Figure 4C:
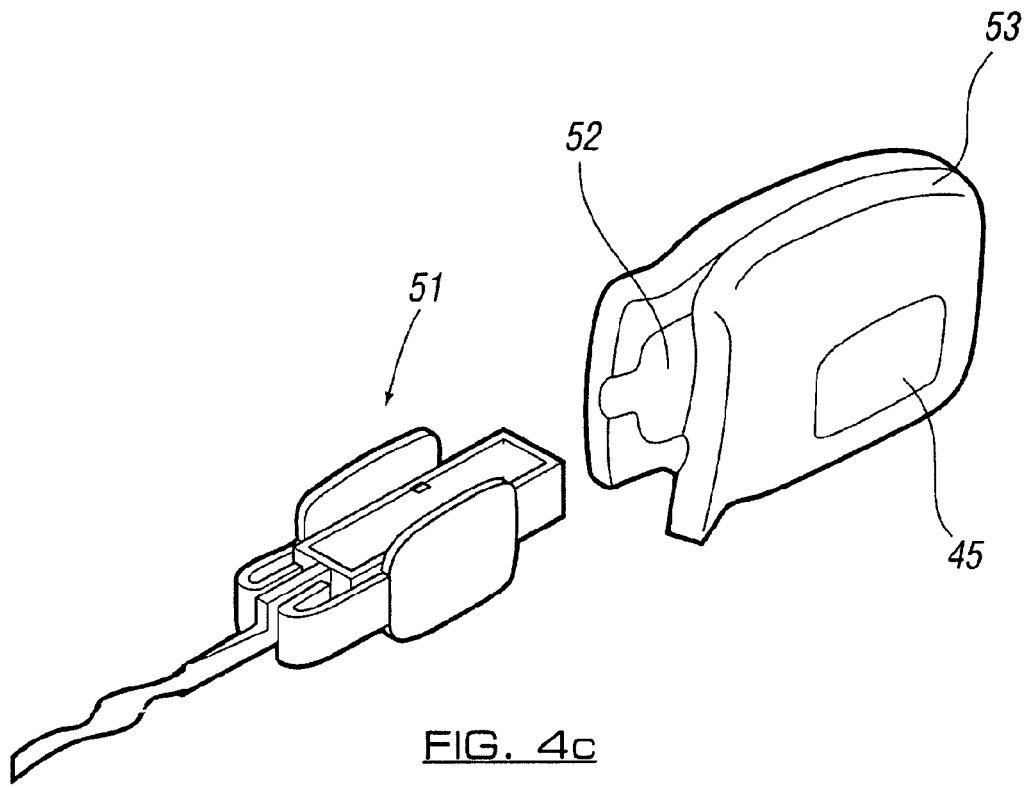

Referring to FIGS. 4(a) (b) and (c) the inner components of the compressible electrode of FIG. 2 are shown prior to assembly of the compressible electrode. The inner components are housed in and/or connected with a chassis (40) which is in electrically connection with external systems via the wire (41) which is used to remove the compressible electrode on completion of the treatment cycle and for connection of the compressible electrode to external power and/or control units. The electrode components (42, 42') have electrode pads (43, 43') that are broadly rectangular in shape. Each pad has an electro-conductive surface (44 and 44' not shown) which is exposed on assembly of the compressible electrode through openings (45 and 45' not shown) of the compressible electrode body shell (53) as shown in FIG. 4(c). Each electrode component (42, 42') has a resilient arcuate arm (46, 46') that at one end (47, 47') is connected to or formed with the pad (43, 43') and at the opposing end (48, 48') is connected to or formed with a flat plate section (49, 49') that is in a plane (A) which is approximately parallel to the plane (B) of the electrode pad (43, 43'). In this embodiment the arcuate arms (46, 46') are connected to the pads (43, 43') at one of their narrower edges. The flat plates (49,49') may be attached to, or located within the chassis (40) as indicated in FIG. 4(b), and in such an arrangement, that the electro-conductive surfaces (44, 44') face away from each other and the chassis (40). In this arrangement the electrode components (42, 42') may be compressed and moved towards the chassis (40) by the application of pressure to the electrode pads (43, 43'). When the pressure is released the electrode components (42, 42') return to their non-compressed state due to the spring like properties afforded to the components by the resilient deformable nature of the arcuate arms (46, 46') in combination with the nature of their attachment to and their spatial arrangement in relation to the chassis (40).

To assemble the compressible electrode the electrode components (42, 42') are attached to the chassis (40) in sprung contact with the ends (49, 49') of the electrode plates. Once combined these components provide a unitary compressible electrode assembly (51) shown in FIG. 4(b) that may then easily be used to manufacture the final compressible electrode. The final compressible electrode is assembled by taking the compressible electrode assembly (51) and compressing the electrode components (42, 42') towards the chassis (40) so that the compressible electrode assembly (51) is in the compressed state. In this state the compressible electrode assembly (51) may then be inserted into a compressible electrode body shell (53) manufactured from biocompatible materials such as a biocompatible foam or compressible material such as a thermoplastic elastomer. The compressible electrode body shell (53) has a cavity (52) that is moulded so that it may accommodate the compressible electrode assembly (51). The compressible electrode body shell (53) has openings (45 and 45' not shown) through which the electro-conductive elements (43, 43') may be exposed to the exterior of the compressible electrode once the compressible electrode assembly (51) has been inserted into the cavity (52) of the compressible electrode body shell (53) and the electrode components (42, 42') are no longer under compression. Once the compressible electrode assembly (51) has been inserted into the compressible electrode body shell (53) then the shell may be welded closed along the open edges to the cavity and also welded around the openings (45, 45') and electrode pads (44, 44'). In an alternative embodiment the compressible electrode assembly (51) in the non-compressed state may be placed in a suitable mould and the compressible electrode body (53) is then formed around the assembly (51) by injection moulding or a similar process. The components by their design and arrangement are easy to assemble and provide an easy to assemble compressible electrode.

In this embodiment the compressible electrode is particularly effective for use in the treatment of anterior and posterior pelvic floor muscle dysfunction due to the combination of a compressible body being used in combination with the compressible electrode assembly having electro-conductive elements that may easily and controllably be compressed as the body is compressed.

Figure 5:
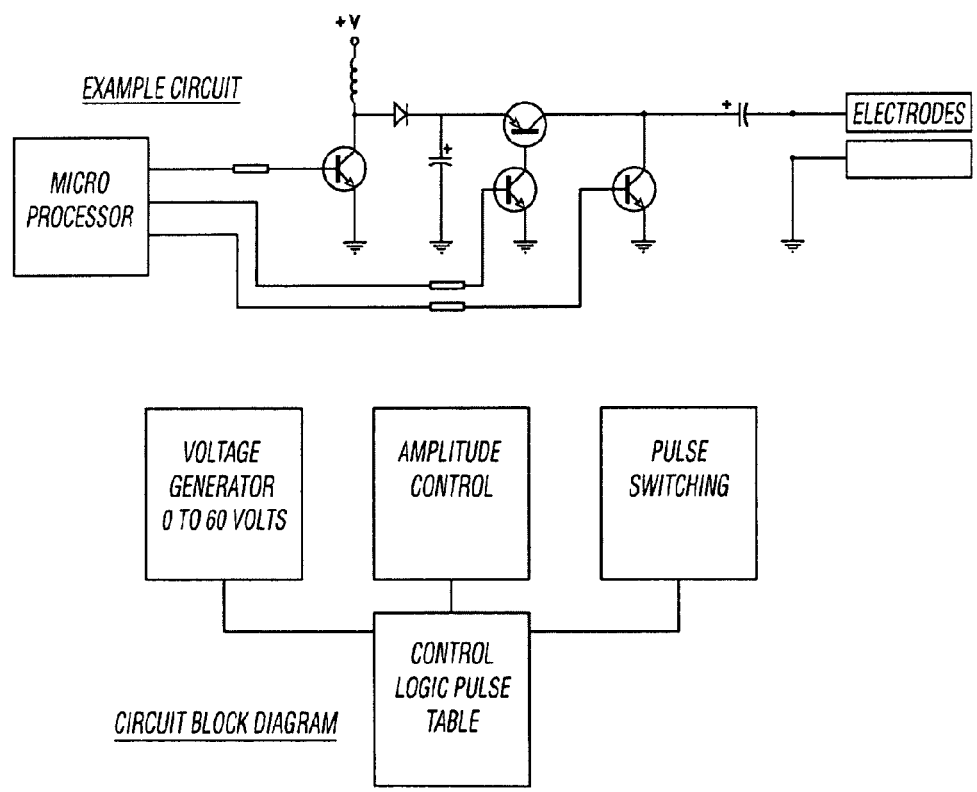
FIG. 5 shows a schematic of and a circuit diagram for a circuit for use with the compressible electrodes of the present invention.

Referring to FIG. 5 there is shown an example of a circuit and a circuit block diagram that may be used in conjunction with the compressible electrode of the present invention. The circuit comprises a voltage generator, means for amplitude control, means for pulse switching and a logical control element (control logic pulse table). Both the power source and control systems are not located within the body of the electrode but are connected to the electrode via a cable connection.

Figure 6:
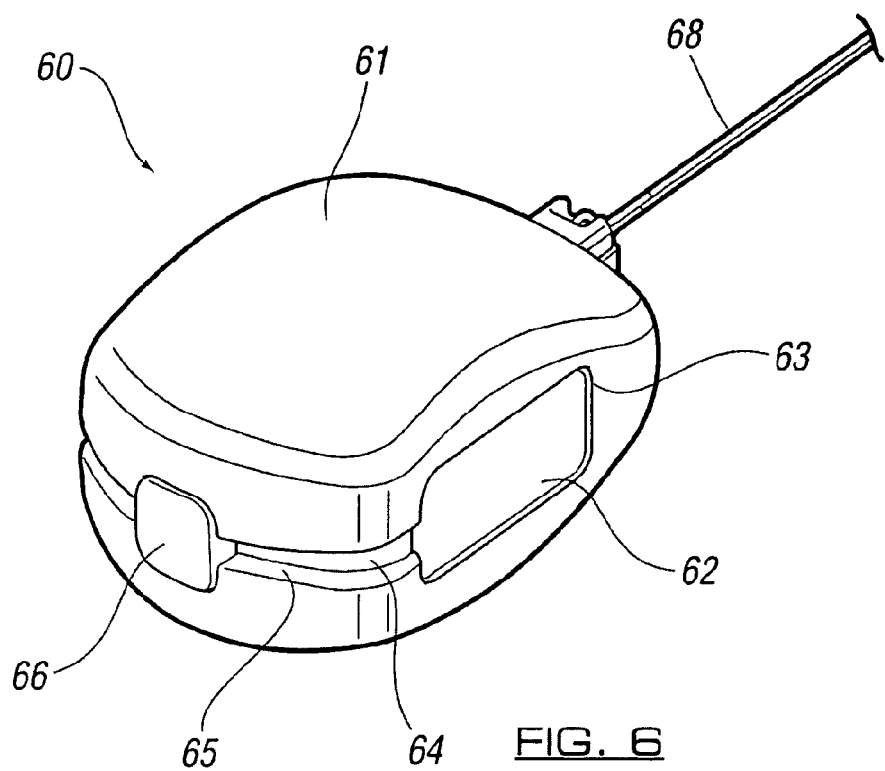
FIG. 6 shows in perspective view an electro-stimulation electrode according to the present invention.

Referring to FIG. 6 an electro-stimulation electrode (60) is shown in the non-compressed, fully expanded state. The electrode (60) has a body (61) which has been constructed from resiliently compressible polyurethane foam. The electro-conductive elements (62 and 62' not shown) are bonded to the surface of the body (61) of the electrode (60) with a suitable adhesive such as a cyanoacrylate based adhesive. The electro-conductive elements (62 and 62' not shown) are located within moulded recesses (63 and 63' not shown). Each electro-conductive element (62 and 62' not shown) has an arm (64 and 64' not shown) which is located within a further arcuate recess (65 and 65' not shown). The ends of these arms (not shown) pass into the interior of the body (61) of the electrode (60) towards the front of the electrode (60) to make contact with suitable connectors located within the interior of the electrode. In this embodiment the ends of the arms (not shown) are partly held in their location by the plug (66) located at the front of the electrode (60). The plug (66) also serves to protect the ends of the arms (not shown). Towards the rear of the electrode is located the wire (68) for connection to the external power and control systems. The wire (68) may be terminated outside of the electrode with a standard connector. The dimensions of this electrode (60) have the same relationships as discussed in detail for electrode (1) illustrated in FIGS. 1 and 1(a). In this embodiment the exposed surfaces of the arms are electrically insulated from the user by means of a suitable polymer film or mask applied to their surface and within the recess.

Figure 7:
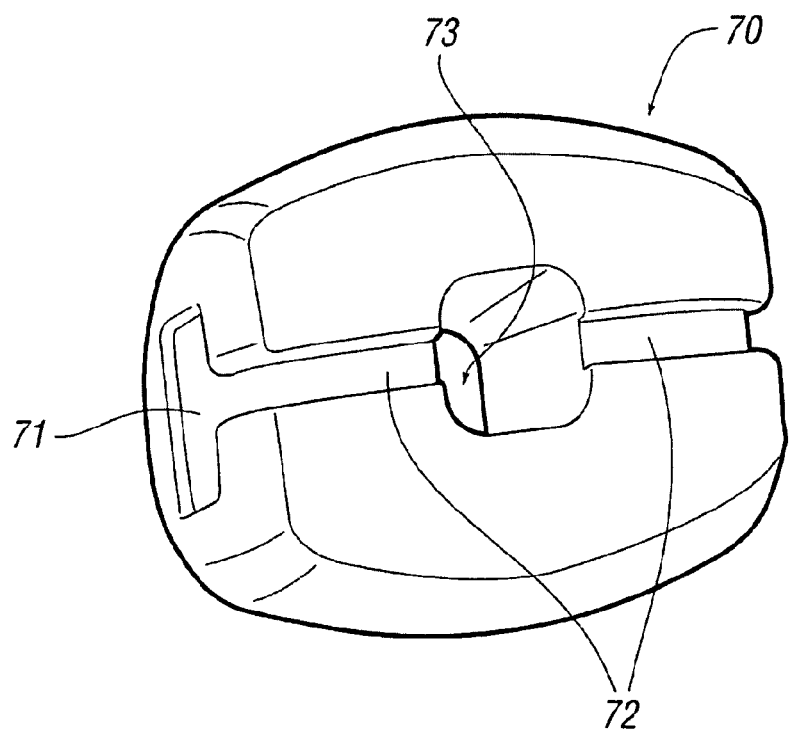
FIG. 7 shows in perspective view the electrode body of the electro-stimulation electrode of FIG. 6.

Referring to FIG. 7 a moulded electro-stimulation electrode body (70) is shown in the non-compressed, fully expanded state but without the internal components or electro-conductive elements. The moulded recesses (71) and (72) for the electro-conductive elements and their arms respectively can clearly be seen. Also show is the internal moulded cavity (73) which is for accommodating the internal electronic sub-assembly (not shown). It can bee seen that the cavity passes through the moulded electrode body with openings at both ends.

Figure 8A:
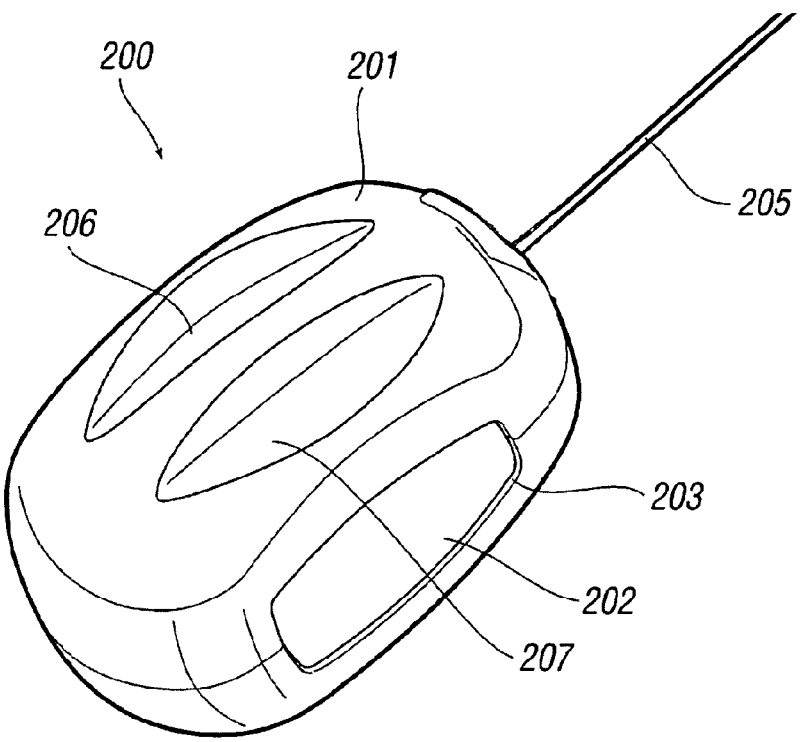
FIG. 8a shows in perspective view an electro-stimulation electrode according to the present invention.
Figure 8B:
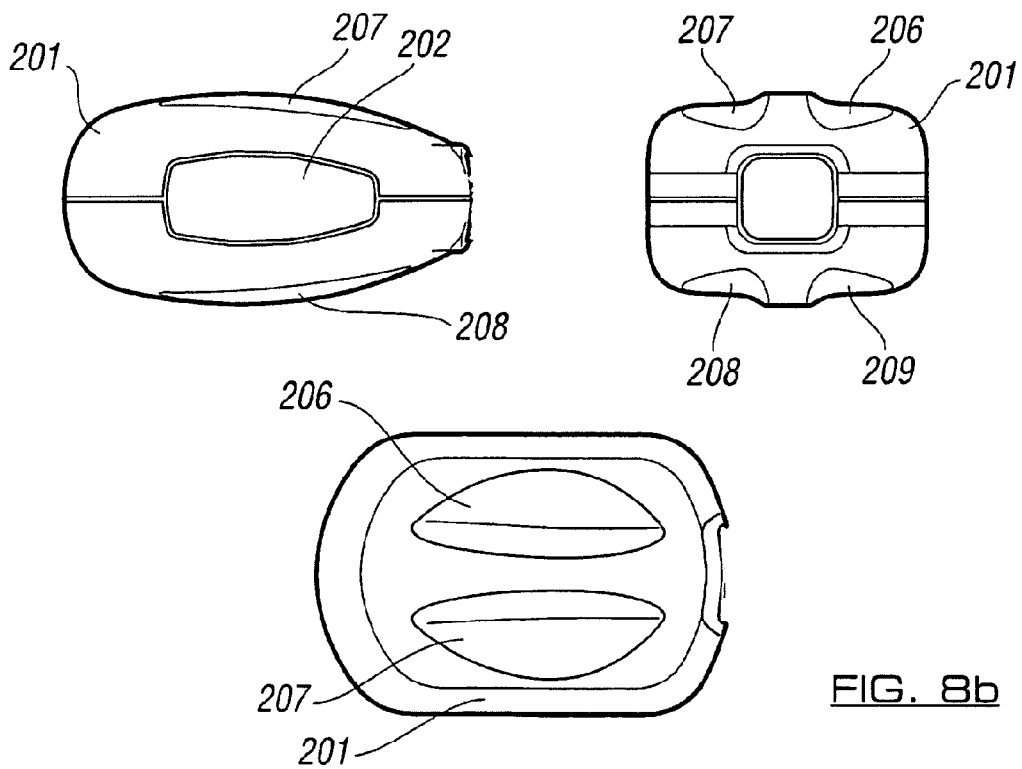
FIG. 8b shows the electrode of FIG. 8a in various elevations.
Figure 10A:
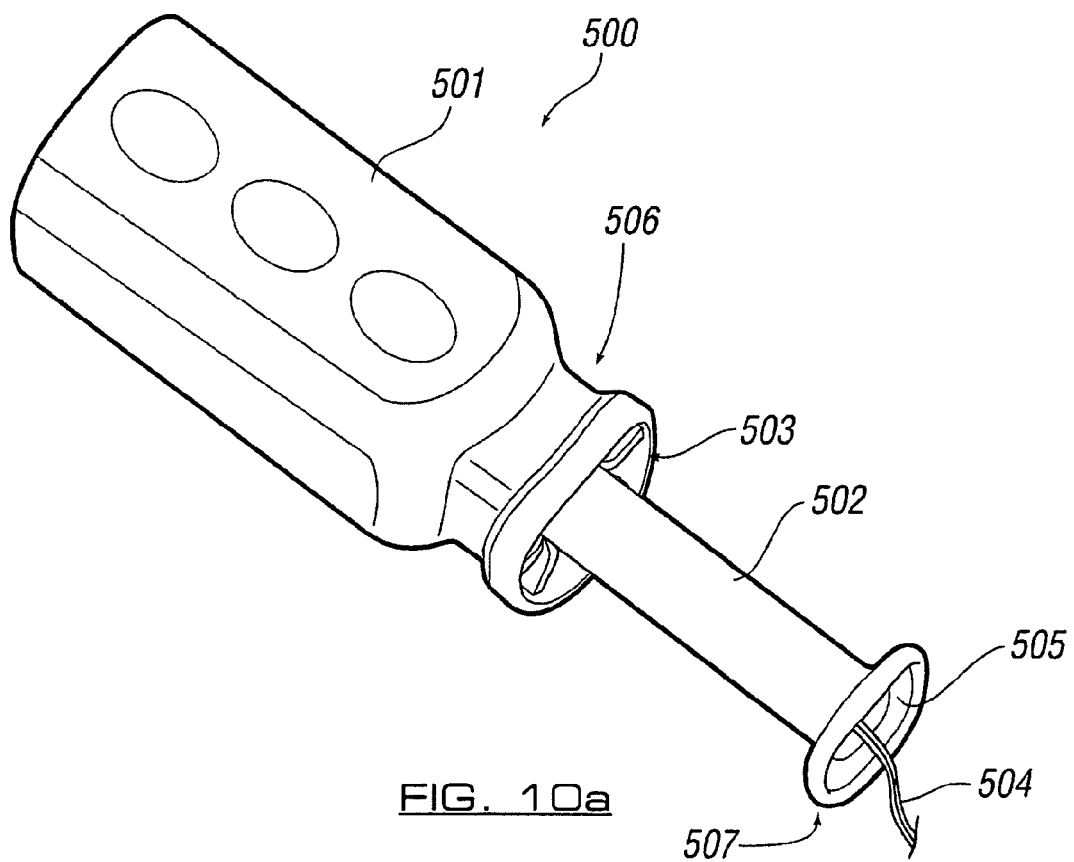

Referring to FIGS. 8a and 8b an electro-stimulation electrode (200) is shown in the non-compressed, fully expanded state. The electrode (200) has a body (201) which has been constructed from injection moulded resiliently compressible polyurethane foam. The electro-conductive elements (202 and 202' not shown) are bonded to the surface of the electrode body (201) with a suitable adhesive such as a cyanoacrylate based adhesive. The electro-conductive elements (202 and 202' not shown) are located within moulded recesses (203 and 203' not shown). Each electro-conductive element (202 and 202' not shown) is connected to wire connectors (not shown) that are attached to clips (not shown) on the back of the electro-conductive elements (202 and 202' not shown). Towards the rear of the electrode is located a wire (205) which connects the electrode to the external power and control units. The electrode body also comprises recesses (206, 207, 208 and 209) in the body surface. These recesses aid compressibility of the electrode. FIG. 10a illustrates the relative proportions of the electrode viewed from the side, top and back of the electrode. The dimensions of this electrode (200) have the same relationships as discussed in detail for electrode (1) illustrated in FIGS. 1 and 1(a).

Figure 9A:
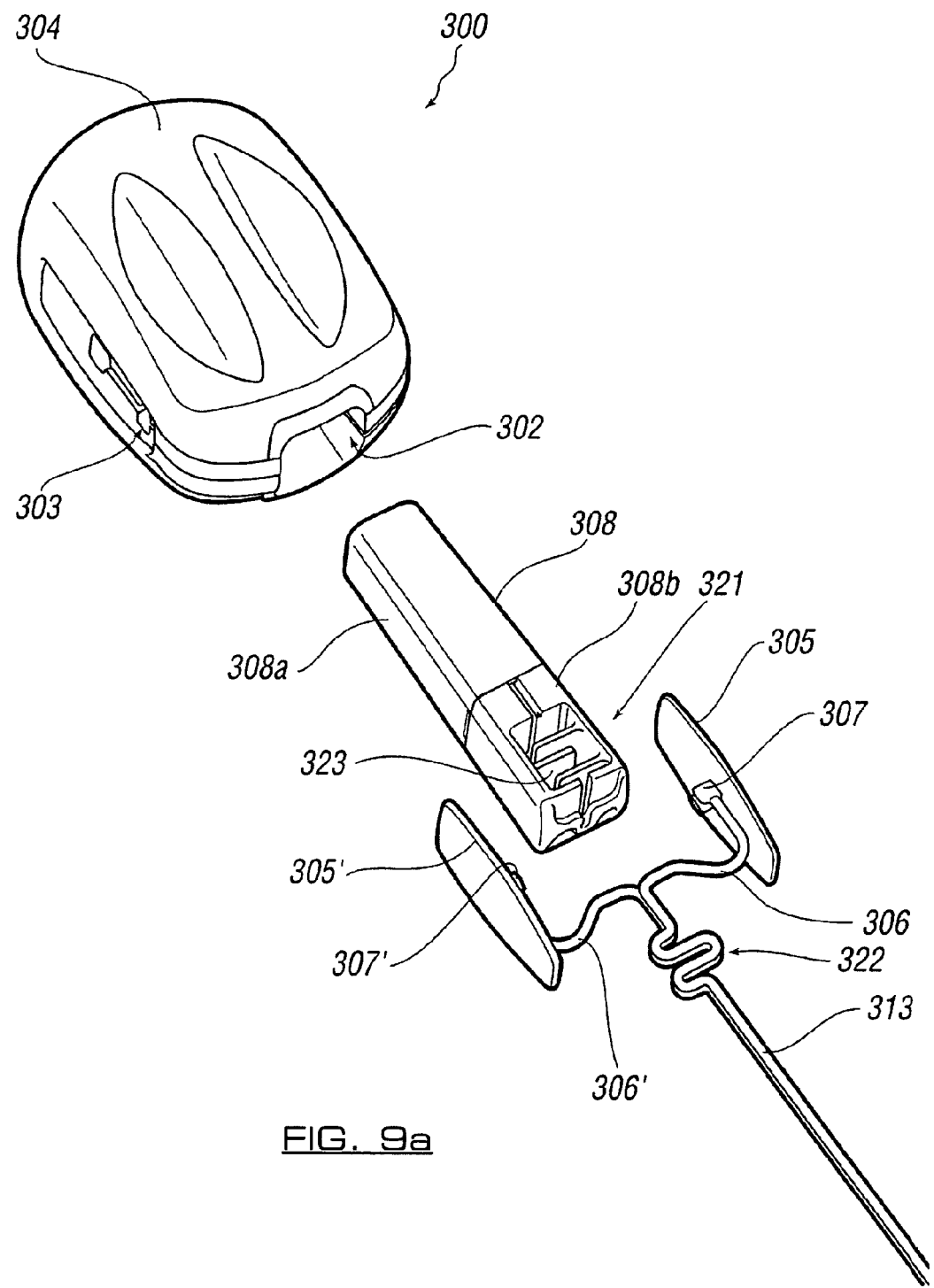
FIG. 9a shows in an exploded perspective view of the components of the electrode of FIG. 8a prior to its assembly.
Figure 9B:
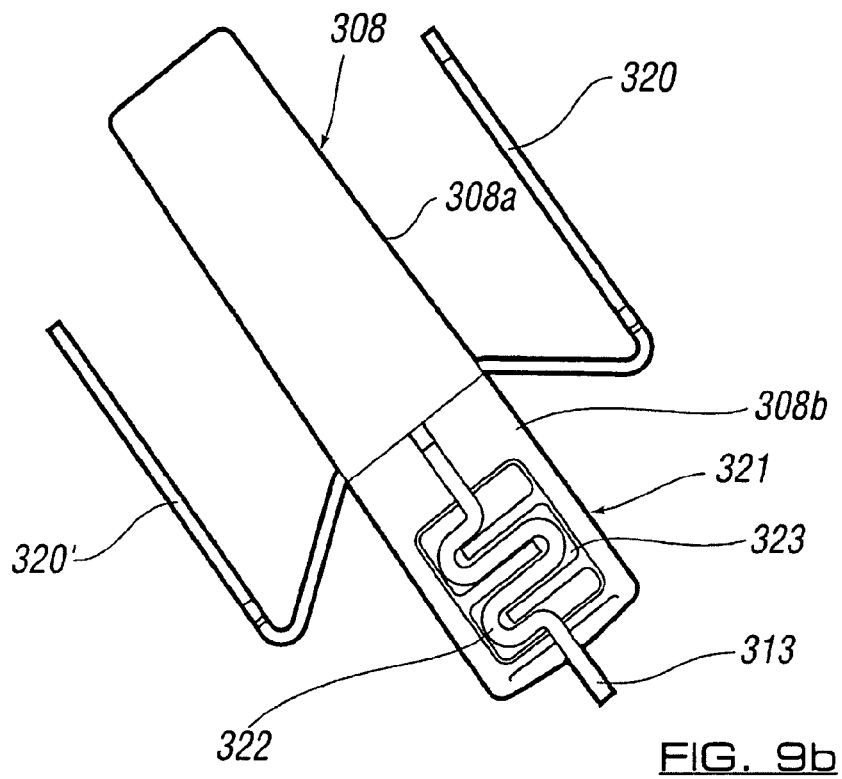
FIG. 9b shows the internal sub-assembly of the device of FIG. 8a, and FIGS. 10(a), (b) and (c) show an applicator arrangement for use with the electro-stimulation electrodes of the present invention.

Referring to FIG. 9a the electro-stimulation electrode of FIGS. 8a and 8b is show in an expanded view illustrating the key components of the electrode (300) prior to its assembly. Unlike the electrode illustrated in FIGS. 6 and 7, the electrode (300) is configured to be assembled through openings a towards the rear (302) and sides (303 and 303' not shown) of the electrode body (304). Unlike the embodiment of FIG. 6 the opening (302) does not pass through to an opening towards the front of the electrode (300). The electro-conductive elements (305 and 305') are clearly shown with conductive wires (306 and 306') clipped to the back of each electroconductive elements (305 and 305') via clips (307 and 307'). During assembly the conductive wires (306 and 306') pass through openings (303 and 303' not shown), pass through the enclosed chassis (308), which is in two parts (308a) and (308b) that may be bonded or snap fitted to each other, and exit from the distal end of the chassis (308) as the wire (313). The electro-conductive elements (305 and 305') and the chassis (308) are bonded in place and to the surface of the electrode body (304) with a suitable adhesive such as a cyanoacrylate based adhesive. The electro-conductive elements (305 and 305') are manufactured from conductive SBS or EVA and are located and bonded within moulded recesses (315 and 315' not shown). FIG. 9b illustrates the spatial relationship if the key components of the sub-assembly after assembly of the electrode as illustrated in FIG. 9a but with the omission of the electrode body (304) for clarity and using electro-conductive elements (320 and 320') that have been manufactured with integral conductive elements making the conductive wires (306 and 306') and clips (307 and 307') illustrated in FIG. 9a redundant. The description for the numerically indicated components in FIG. 9b is the same as that used for like numbered components of FIG. 9a. FIGS. 9a and 9b show the chassis section (308b) with a moulded strain relief mechanism (321) for the wire (313). This strain relief enables the use of the wire to remove the electrode after use. On assembly of the electrode (300) the wire (322) follows this tortuous path (323) of the strain mechanism (321) before passing through internal passages to be connected to the electro-conductive elements.

Figure 10B:
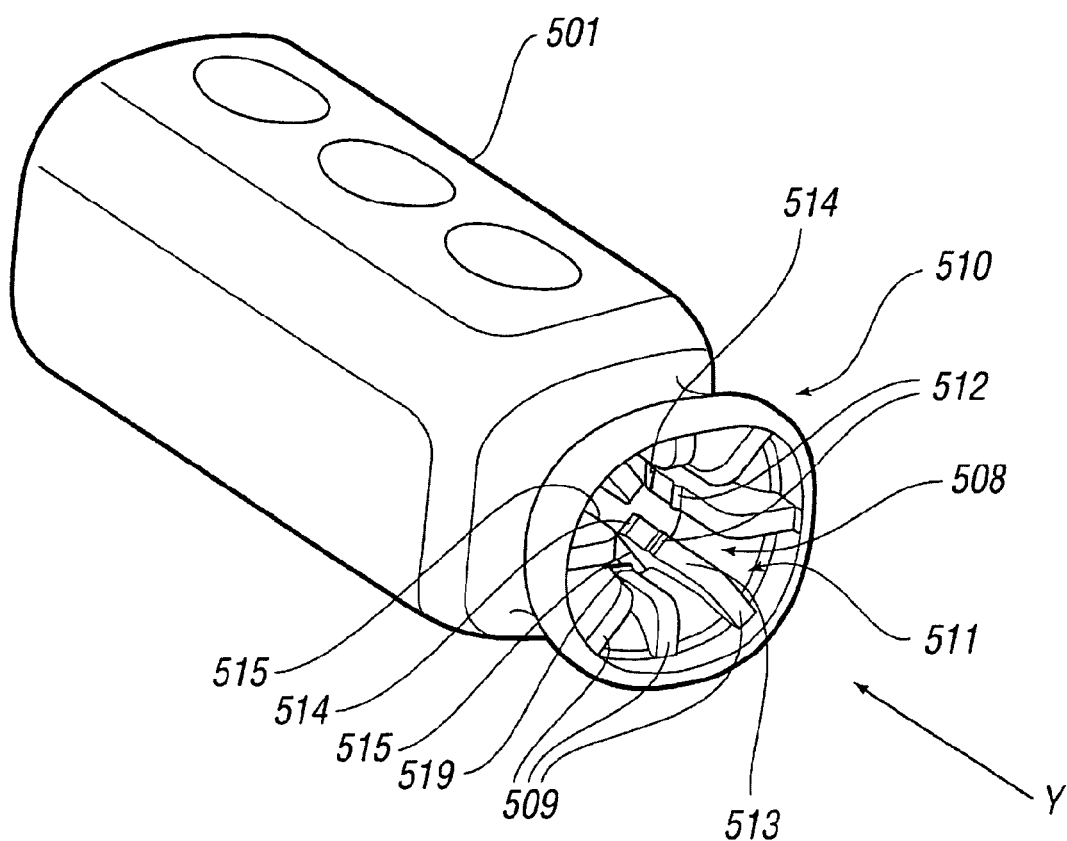
Figure 10C:
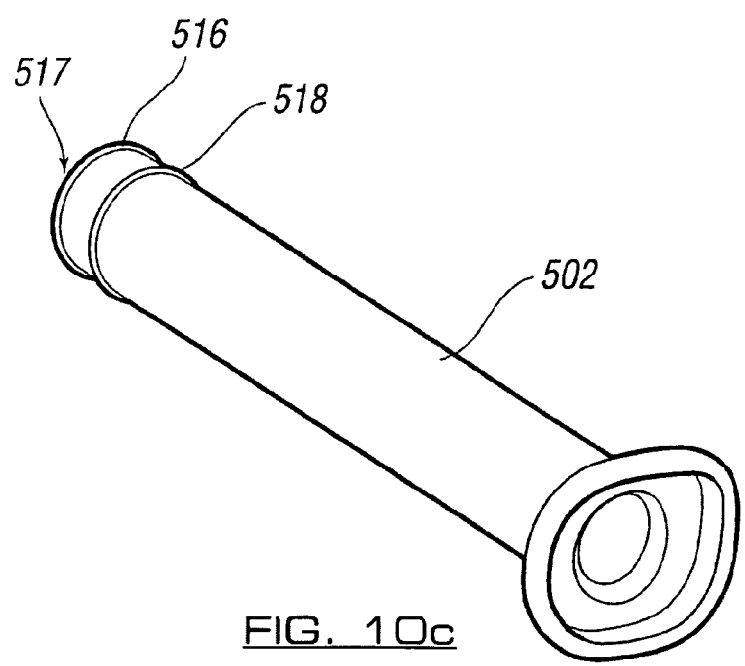

A further suitable form of applicator for the purpose of deployment of the electrode of the present invention is illustrated in FIGS. 10a to 10d. Referring to FIG. 10a there is shown an applicator (500) that has an outer member (501) and an inner member (502). The inner member (502) takes the form of a hollow cylinder which is engaged with the distal end (503) of the outer member (501). The applicator in this state has an electro-stimulation electrode (not shown) within the bore (not shown) of the outer member (501). The wire (504) of the device is shown passing through the bore of the inner member (502) and exiting through the bore opening (505) of the inner member (501). The outer member (501) has a gripping region (506) that is shaped to aid holding and actuation of the applicator (500) by the human hand. The inner member (502) has a flanged end (507) that presents a larger surface area to aid application of pressure by a human hand to the inner member (502) during use of the applicator (500). This applicator (500) is operated in a similar fashion to that described in FIGS. 3a and 3b. With reference to FIG. 10b the outer member (501) is shown without the inner member (502). This figure clearly shows the detent mechanism (508) which is exposed towards rear of the member (501). This detent mechanism (508) consists of a series of spaced apart fins (509) each attached at the distal end (510) of the outer member on its interior radial surface (511). The fins (509) protrude towards the central axis (Y) of the outer member (501). Each of the fins (509) has a ridge (512) on their inner surface (513) which, in this embodiment, is aligned with the ridges (512) on each neighbouring fin (509). In addition there is a chamfer surface (514) provided at the junction of the proximate edge (515) of each fin and their inner surface (513). This fin (509), ridge (512) and chamfer surface (514) arrangement provides a detent mechanism with corresponding features on the inner member (502) and a narrow bore within the outer member (510) to accommodate, secure and support the inner member (502) within the outer member (501) once the applicator (500) has been assembled. With reference to FIG. 10c the inner member (502) has an annular ridge (516) around its external circumference at its proximate end (517) and an annular notch (518) on the same surface and close to the annular ridge (516). The distance between the annular ridge (516) and annular notch (518) on the inner member (512) corresponds to the distance between the ridges (512) and chamfer surface (514) on each fin (509) of the outer member (501). Thus when the inner member (502) is inserted into the outer member (501) it is held in the correct axial position by the radial fin (509) arrangement and is securely held by the engagement of its notch (518) and ridge (516) with the corresponding ridge (512) and chamfer surface (514) of the outer member fins (509). In an alternative embodiment the radial notch (518) of the inner member (502) is replaced with a distal radial ridge. In this embodiment the distance between the proximate and radial ridges of the inner member (502) is just greater than the distance between the chamfer surface (514) and ridge (512) arrangement of the outer member (501). On assembly the proximate ridge (516) of the inner member (502) engages with the chamfer surface (514) and the distal radial ridge (518' not shown) impacts the frusto-conical surface (519) on the ridges (512) of the fins (509). For both embodiments on insertion of the inner member (502) into the outer member (502) these arrangements of ridges and notches engage with each other to provide the required detent effect.

All of the features disclosed in this specification for each and every embodiment (including any accompanying claims, abstract and drawings), and/or all of the steps of any method or process so disclosed, may be combined in any combination, except combinations where at least some of such features and/or steps are mutually exclusive.

The invention claimed is:

1. A compressible vaginal or anal electro-stimulation electrode for the neuromuscular electro-stimulation of the musculature of the pelvic floor complex, which comprises a deformable body of resiliently compressible foam material and at least two electro-conductive elements located at or on the external surface of the body, wherein the electrode body has two dimensions perpendicular to the axis of insertion that are of different dimension and different degrees of compressibility and may be reduced under compression of the foam body to dimensions that are reduced on compression by at least 15% and wherein the body is not freely rotatable about the axis of insertion when in-situ.

2. The electrode of claim 1, wherein the body is compressible due to a combination of the use of a resiliently deformable/compressible material for its manufacture and the nature of the electrode structure.

3. The electrode of claim 2, wherein the body is manufactured from resiliently deformable/compressible material and the interior of the electrode body is hollow.

4. The electrode of claim 1, wherein the body of the compressible electrode is moulded around the interior components of the compressible electrode to encapsulate them.

5. The electrode of claim 1, wherein the body has a hollow interior into which the interior components are placed during manufacture of the compressible electrode.

6. The electrode of claim 1, wherein the dimensions of the electrode body are greater along the axis of insertion compared to the dimensions perpendicular to that axis.

7. The electrode of claim 1, wherein the compressible electrode is compressed to relative dimensions that are different in proportion to the dimensions of the electrode in the non-compressed state.

8. The electrode of claim 1, wherein in the non-compressed state the electrode has a length in the range of from 30 to 120 mm.

9. The electrode of claim 1, wherein in the non-compressed state the electrode has at least two equal dimensions or at least two non-equal dimensions perpendicular to the axis of insertion that are within the range of 30 to 60 mm.

10. The electrode of claim 1, wherein the length of the electrode in the non-compressed state is equal to the length of the electro-stimulation electrode in the compressed state.

11. The electrode of claim 1, wherein at least one of the dimensions of the electrode perpendicular to the axis of insertion are reduced on compression by at least 20%.

12. The electrode of claim 1, wherein the volume of the electrode in the compressed state is reduced by at least 20% compared to that in the non-compressed state.

13. The electrode of claim 1, wherein in the compressed state the dimensions of the electrode perpendicular to the axis of insertion are such that the width is in the range of 10 to 35 mm, and the height of the compressed electrode is within the range of 10 to 40 mm.

14. The electrode of claim 1, wherein the shape of the compressible electrode in the compressed form approximates to that of a tampon.

15. A compressible electrode as claimed in claim 1 further comprising an applicator for deployment of the compressible electrode, wherein the electrode is adapted for deployment into an anal or vaginal endocavity by
   a. positioning of an applicator containing said electrode in compressed form at the opening of the vagina or anus, and
   b. discharge of the electrode from the applicator into the vagina or anus allowing expansion of the electrode within the vagina or anus.

16. An electrode as claimed in claim 15 wherein the applicator has a hollow body to accommodate the compressed electrode.

17. An electrode kit for the stimulation of the musculature of the pelvic floor complex which comprises a compressible electrode in combination with an applicator comprising an outer member and an inner member, the electrode being located within the outer member.

18. The electrode of claim 1, wherein the electro-conductive elements are formed as part of interior components of the electrode and are exposed at the surface of the body of the electrode through defined orifices in the body.

19. The electrode of claim 1, wherein electro-conductive elements are approximately rectangular of approximate dimensions of 28 mm×13 mm and are located at or upon opposite surfaces of the compressible electrode approximately 180 degrees apart.

20. The electrode of claim 1, wherein the electro-conductive elements are annular.

21. A method of stimulating the musculature of the pelvic floor complex, which method comprises providing stimulation to the musculature of the pelvic floor using a compressible electrode according to claim 1, with a treatment cycle waveform.

22. A method as claimed in claim 21 wherein the stimulation is for the treatment for anterior and posterior pelvic floor muscle dysfunction.

23. A method as claimed in claim 21 wherein the waveform used comprises two or more components each component being a train of regularly spaced pulses.

24. A method as claimed in claim 23, wherein the second component is combined with the first component but the second component has spacing between successive pulses that is less than the spacing between successive pulses in the first component.

25. A method as claimed in claim 23 wherein there is a third component that has spacing between successive pulses that is less than the spacing between successive pulses in the second component.

26. A method as claimed in claim 23, wherein there are periods of relaxation between sets of pulse trains.

27. A method as claimed in claim 26, wherein period of relaxation is equal to or greater than the period of stimulation.

28. A method as claimed in claim 21 wherein the treatment cycle is 3 hours or less.

29. A method as claimed in claim 28, wherein the treatment cycle is 2 hours or less.

30. A method as claimed in claim 28, wherein the treatment cycle is 1 hour or less.

31. A method as claimed in claim 28, wherein the treatment cycle is less than 1 hour.

32. A method as claimed in claim 28, wherein the treatment cycle is 45 minutes or less.

33. A method as claimed in claim 23, wherein the first component has a pulse repetition frequency between 1 and 15 Hz, wherein the second component has a pulse repetition frequency between 30 and 60 Hz.

34. A method as claimed in claim 23 wherein the pulses have a pulse width of 50 to 350 microseconds.

35. A method as claimed in claim 24 wherein the pulse width may be varied during use of the electrode.

36. A method as claimed in claim 24 wherein the amplitude of the pulses for each component is of the same magnitude.

37. A method as claimed in claim 24 wherein the amplitude of the pulses for each component is of different magnitude.

38. A method as claimed in claim 24 wherein the pulse amplitude for one or more of the components is varied at one or more points in time throughout the treatment cycle.

39. A method as claimed in claim 24 wherein at least one component consists of a series of pulses of pulse width 150 to 350 microseconds at a maximum voltage of 60 volts, and between each sequence of pulses there is a period or rest of between 5 to 10 seconds.

40. A method as claimed in claim 21 wherein the current is applied regulated and increased throughout a treatment period.

41. A method as claimed in claim 21, wherein the treatment cycle is started at less than 45 mA and rises to 45 mA or more for the last ten minutes of the treatment cycle with a series of ramps in between.

42. A method as claimed in claim 21 wherein at a pulse frequency of 35 Hz and pulse width of 250 microseconds, the current is applied at 6 mA and rises to 12 mA over the first 10 minutes, then the current is ramped from 12 mA to 40 mA over the next 10 minutes, then the current is held at 40 mA over the next 10 to 15 minutes.

43. A method as claimed in claim 21 wherein the third component has a pulse repetition frequency between 80 and 300 Hz.

44. The electrode of claim 1, wherein the body of the device when viewed in a cross-section taken perpendicular to the axis of insertion into the anus or vagina is non-circular.

* * * * *

UNITED STATES PATENT AND TRADEMARK OFFICE
CERTIFICATE OF CORRECTION

| | | |
|---|---|---|
| PATENT NO. | : 8,805,509 B2 | Page 1 of 1 |
| APPLICATION NO. | : 12/094948 | |
| DATED | : August 12, 2014 | |
| INVENTOR(S) | : Boyd et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 961 days.

Signed and Sealed this
Eleventh Day of August, 2015

Michelle K. Lee
*Director of the United States Patent and Trademark Office*